US012797261B2

(12) United States Patent
Kishida

(10) Patent No.: US 12,797,261 B2
(45) Date of Patent: Nov. 17, 2026

(54) UNDERPANTS-TYPE DISPOSABLE WEARING ARTICLE

(71) Applicant: DAIO PAPER CORPORATION, Ehime (JP)

(72) Inventor: Keisuke Kishida, Tochigi (JP)

(73) Assignee: Daio Paper Corporation, Ehime (JP)

( * ) Notice: Subject to any disclaimer, the term of this patent is extended or adjusted under 35 U.S.C. 154(b) by 284 days.

(21) Appl. No.: 18/551,566

(22) PCT Filed: Mar. 24, 2022

(86) PCT No.: PCT/JP2022/014095
§ 371 (c)(1),
(2) Date: Sep. 20, 2023

(87) PCT Pub. No.: WO2023/026560
PCT Pub. Date: Mar. 2, 2023

(65) Prior Publication Data

US 2024/0173176 A1 May 30, 2024

(30) Foreign Application Priority Data

Aug. 26, 2021 (JP) ................................ 2021-138050

(51) Int. Cl.
*A61F 13/15* (2006.01)
*A61F 13/49* (2006.01)
(Continued)

(52) U.S. Cl.
CPC .... *A61F 13/49001* (2013.01); *A61F 13/4902* (2013.01); *A61F 13/49017* (2013.01); *A61F 13/496* (2013.01); *A61F 13/5323* (2013.01)

(58) Field of Classification Search
CPC ............ A61F 13/49001; A61F 13/4902; A61F 13/49017; A61F 13/496; A61F 13/5323
See application file for complete search history.

(56) References Cited

U.S. PATENT DOCUMENTS

2007/0255245 A1* 11/2007 Asp ........................ A61F 13/496 604/385.24
2013/0102982 A1* 4/2013 Nakano ............. A61F 13/49001 604/385.24
(Continued)

FOREIGN PATENT DOCUMENTS

CN 101090681 A 12/2007
CN 102958483 A 3/2013
(Continued)

OTHER PUBLICATIONS

International Search Report for PCT/JP2022/014095, dated Jun. 14, 2022.
(Continued)

*Primary Examiner* — Jacqueline F Stephens
(74) *Attorney, Agent, or Firm* — Andrus Intellectual Property Law, LLP

(57) ABSTRACT

An underpants-type disposable diaper has a back body part including a pair of first portions, and a second portion located in range of a center line passing through a center of the back body part. An intergluteal cleft stretchable region is provided over the second portion. Side edges of the intergluteal cleft stretchable region are away from both imaginary straight lines to a center side thereof. A maximum elongation in the width direction of the intergluteal cleft stretchable region is larger than in the width direction of a region, which is adjacent to the intergluteal cleft stretchable region on both sides thereof. The absorber, at both the sides of the intergluteal cleft stretchable region in the width direction, has slots formed to extend outwardly in the width direction toward a back side, respectively.

14 Claims, 26 Drawing Sheets

(51) Int. Cl.
*A61F 13/496* (2006.01)
*A61F 13/532* (2006.01)

(56) References Cited

U.S. PATENT DOCUMENTS

| | | | | |
|---|---|---|---|---|
| 2014/0163500 | A1* | 6/2014 | Roe | A61F 13/49001 604/374 |
| 2018/0014984 | A1* | 1/2018 | Sakai | B29C 66/344 |
| 2018/0015709 | A1 | 1/2018 | Takeuchi | |

FOREIGN PATENT DOCUMENTS

| | | | |
|---|---|---|---|
| CN | 104853704 | A | 8/2015 |
| CN | 107970092 | A | 5/2018 |
| JP | 2008-521481 | | 6/2008 |
| JP | 2012-10905 | | 1/2012 |
| JP | 2012-10951 | | 1/2012 |
| JP | 2015-104542 | | 6/2015 |
| JP | 2015142685 | A | 8/2015 |
| JP | 5967735 | B1 | 8/2016 |
| JP | 2016-187386 | | 11/2016 |
| JP | 2018-82853 | | 5/2018 |
| JP | 2020-48906 | | 4/2020 |
| WO | 2015/076136 | | 5/2015 |
| WO | 2017105521 | A1 | 6/2017 |

OTHER PUBLICATIONS

Extended European Search Report for EP Patent Appl. No. 22860858.4, dated Jul. 14, 2025.
Office Action for CN Patent Appl. No. 202280022319.7, dated May 21, 2026.

* cited by examiner

[FIG.1]
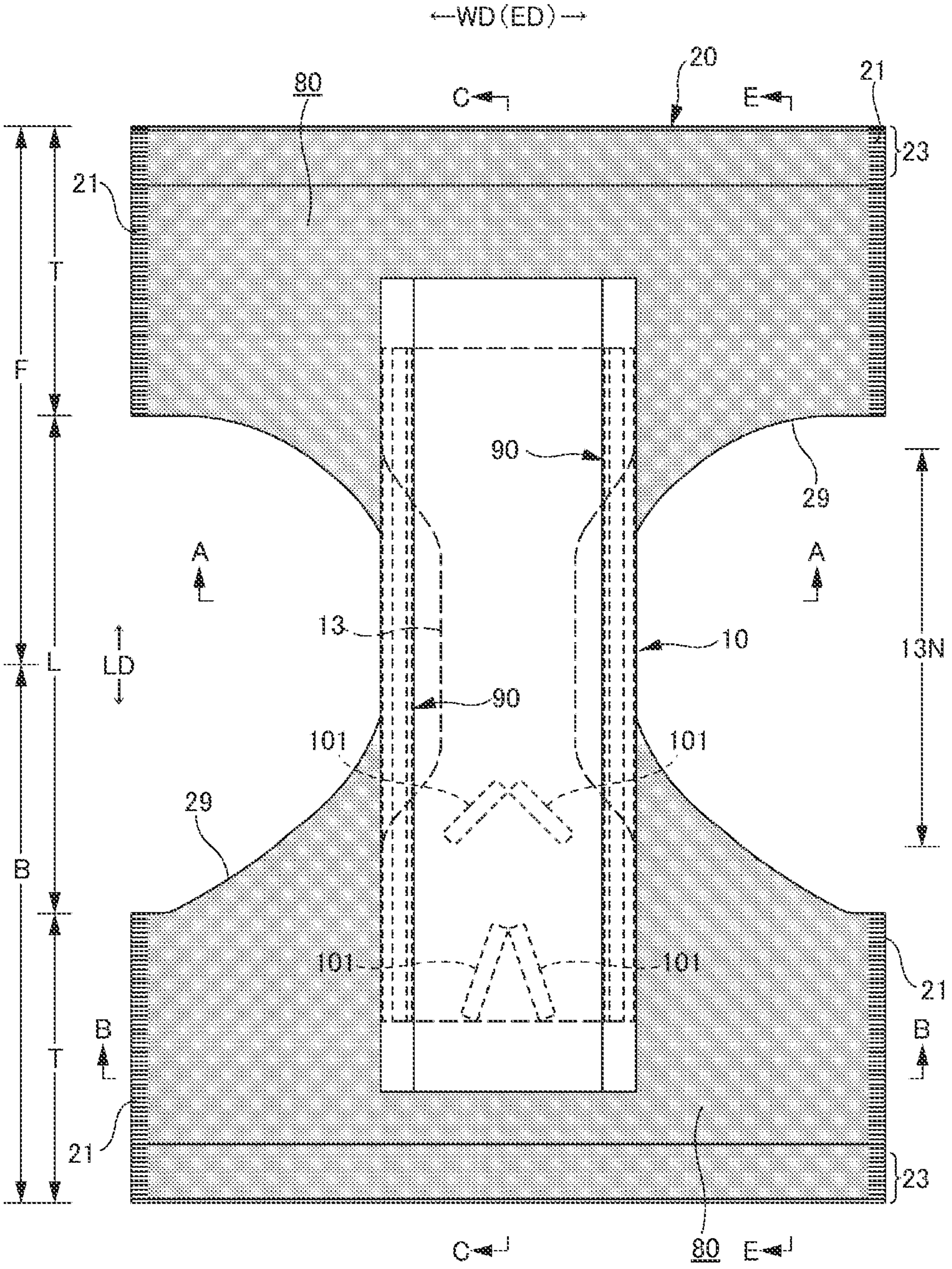

[FIG.2]
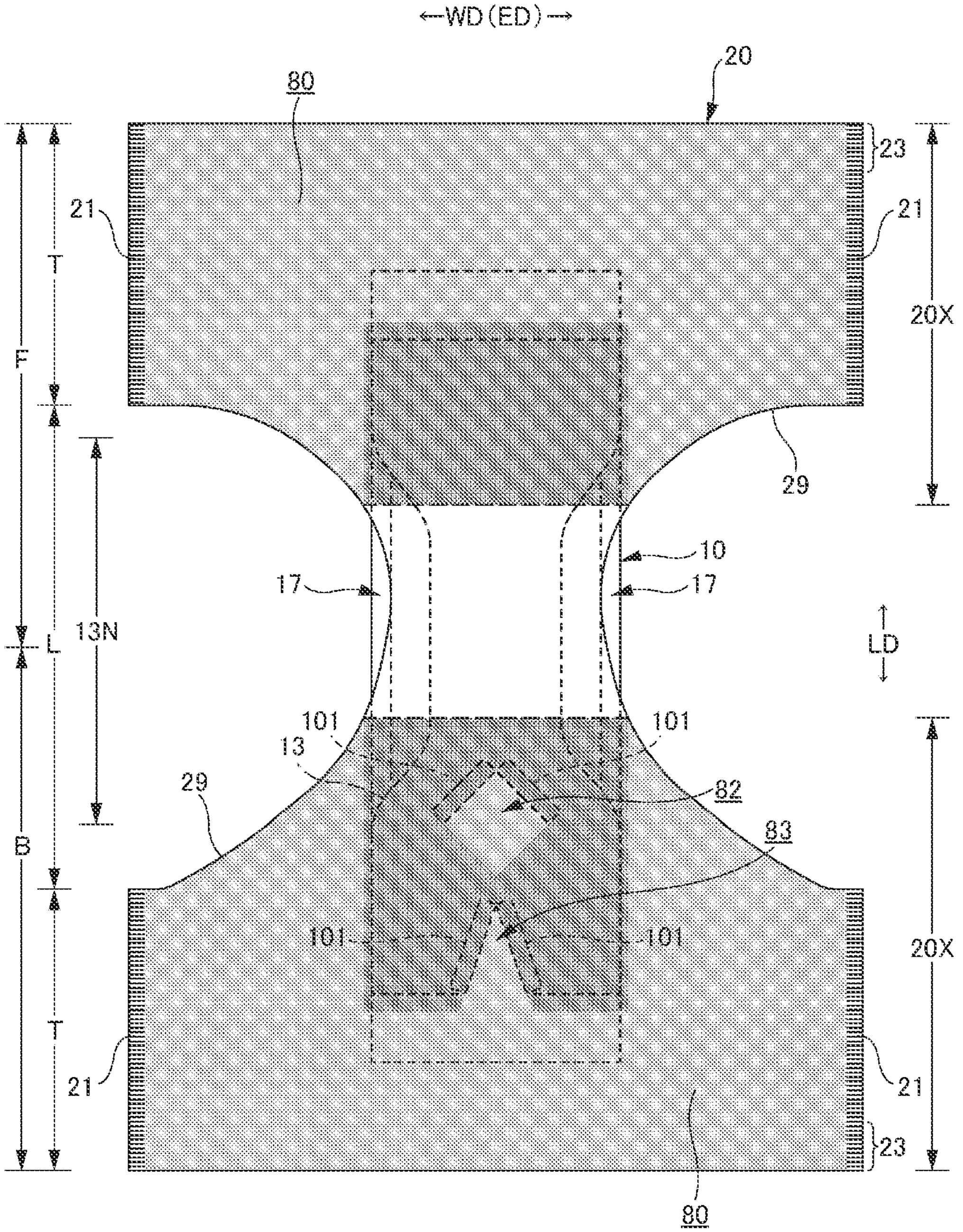

[FIG.3]
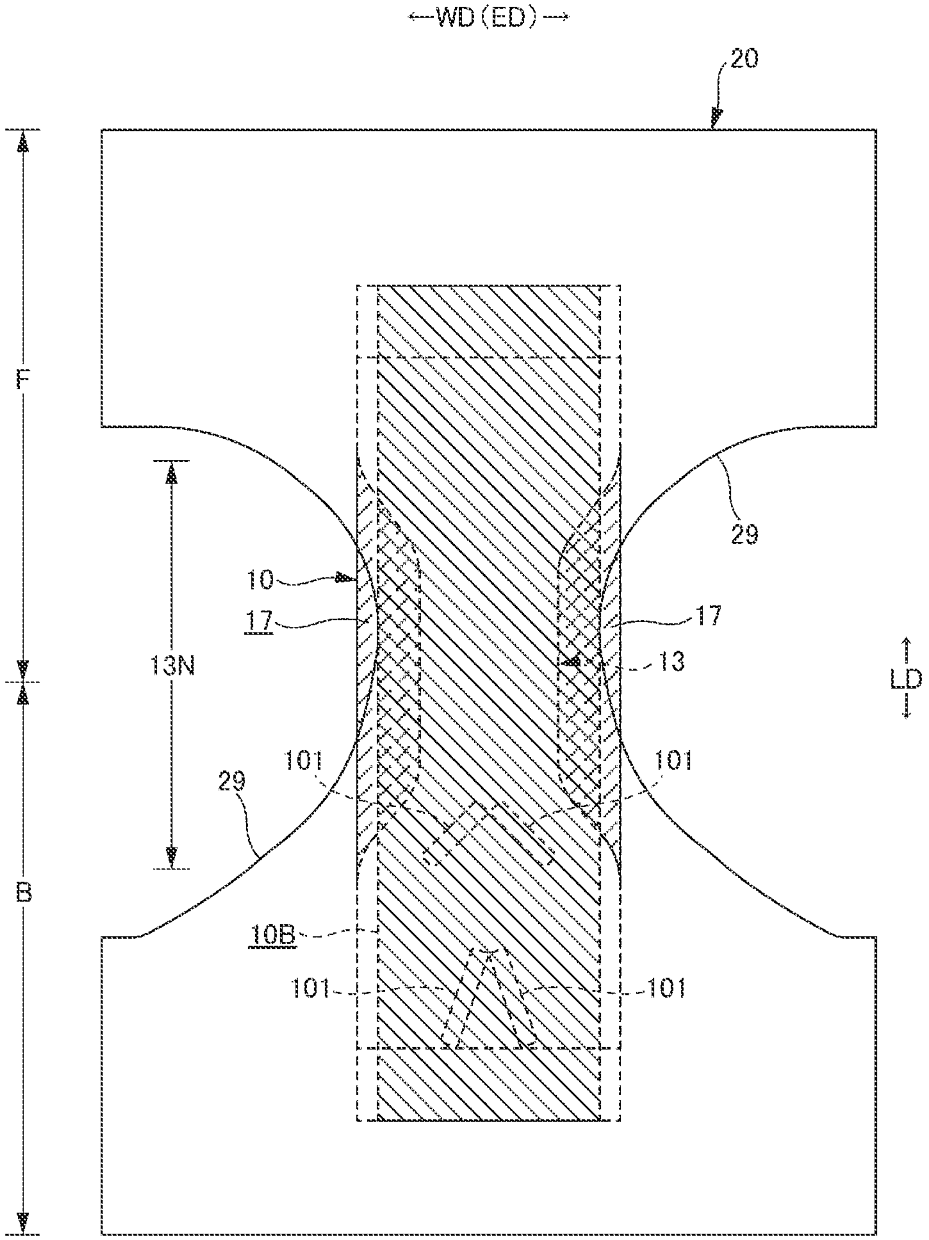

[FIG.4]
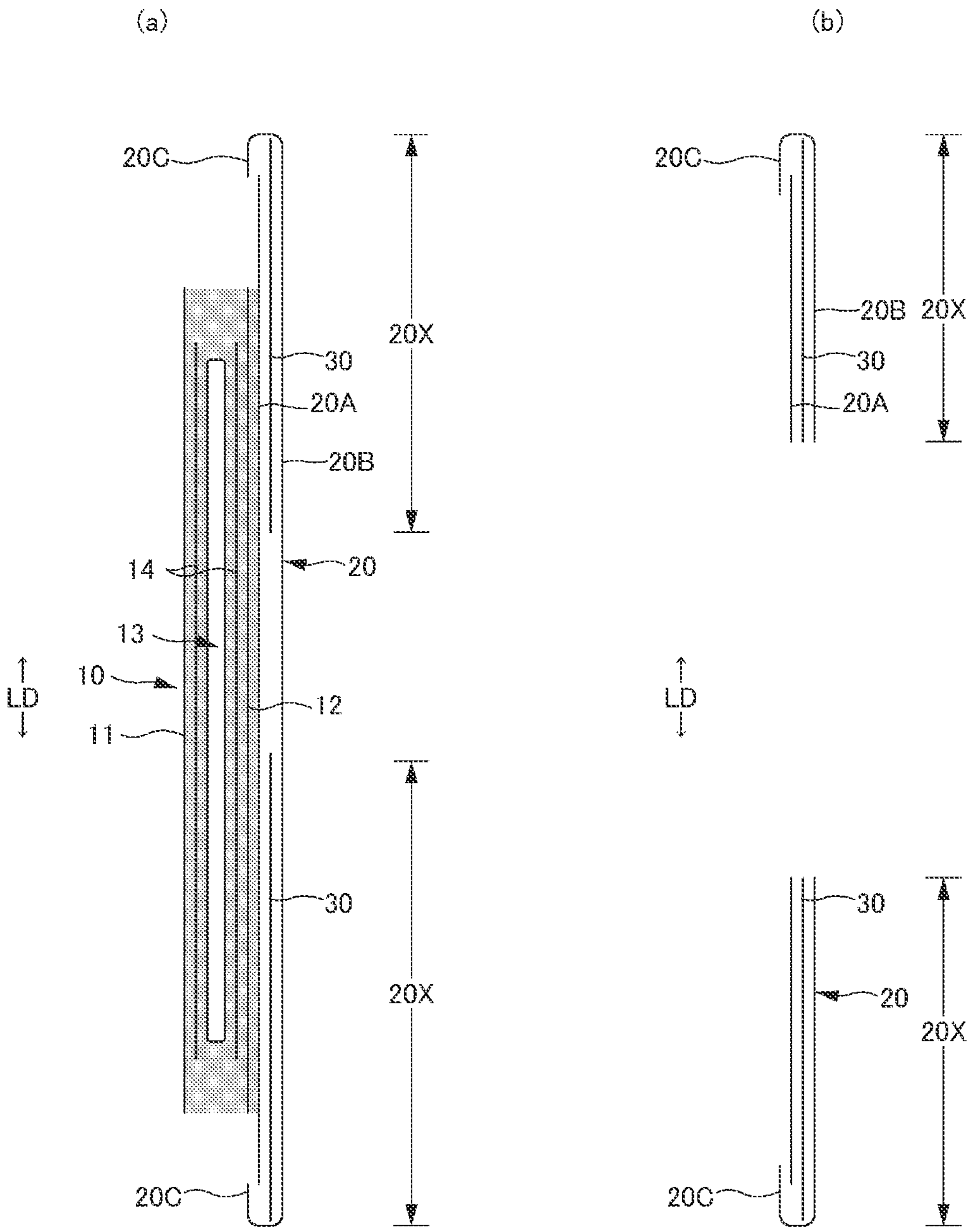

【FIG.5】
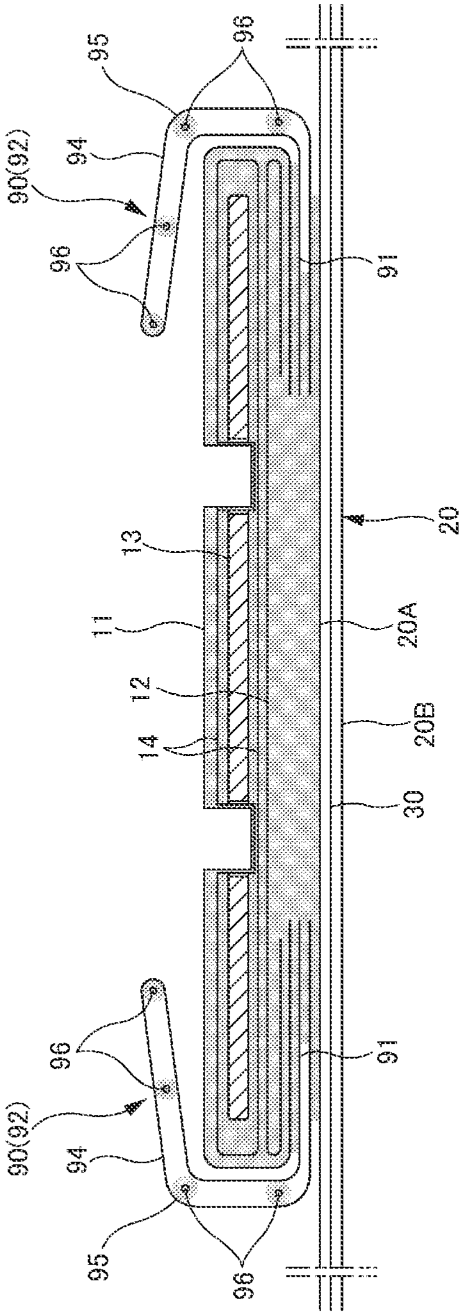

【FIG.6】
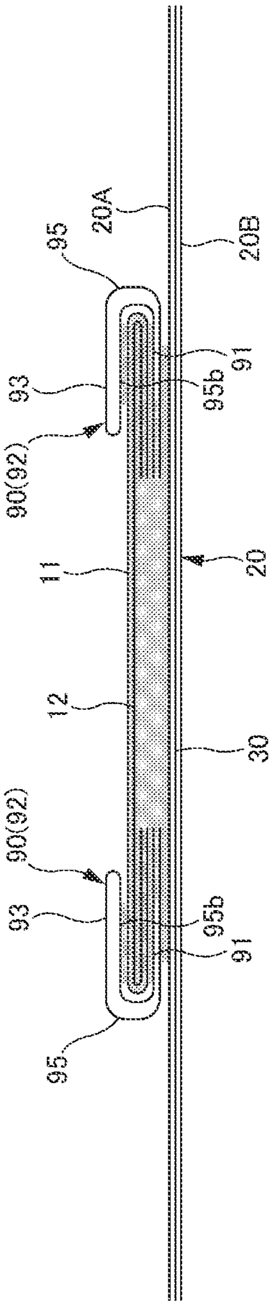

[FIG.7]
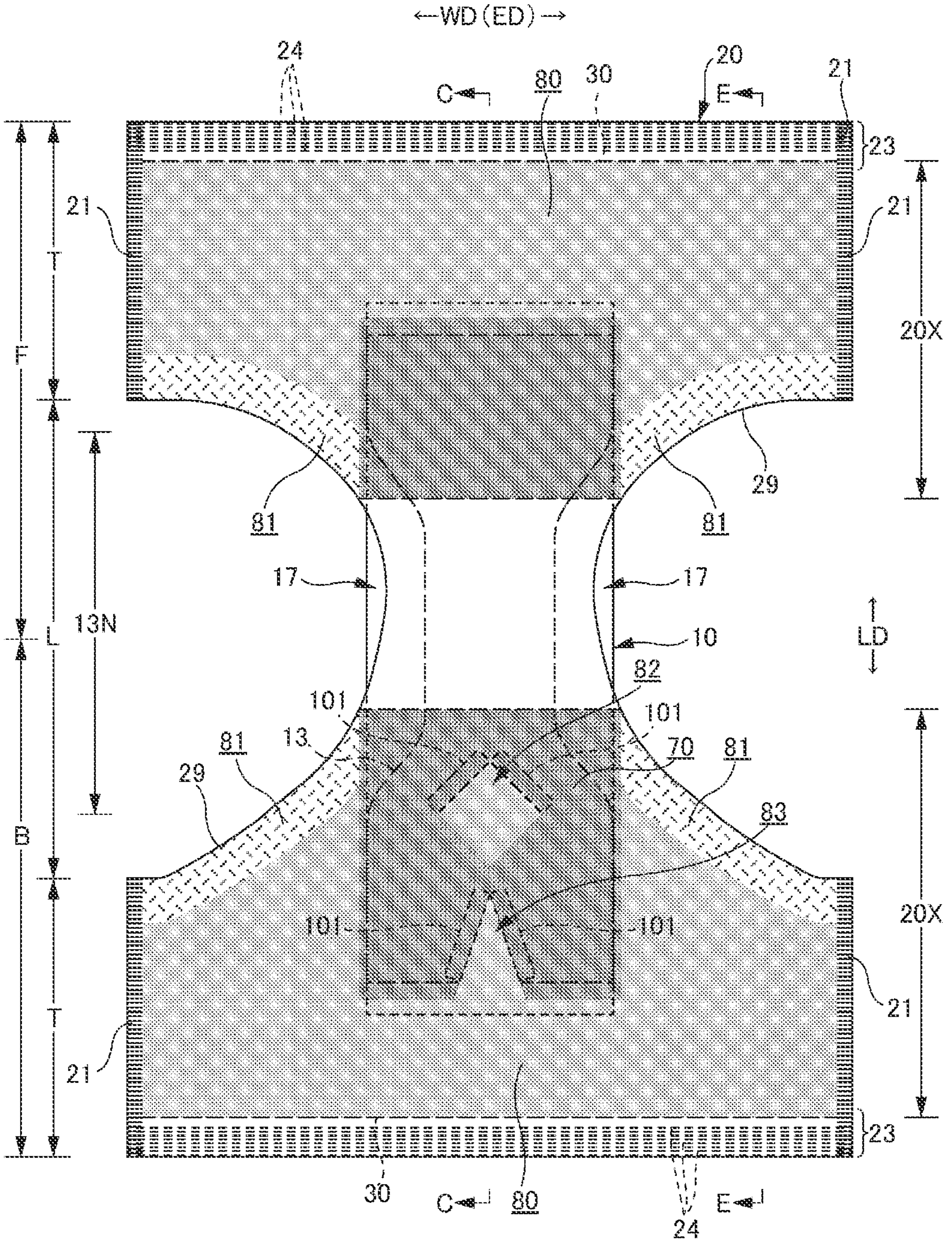

[FIG.8]
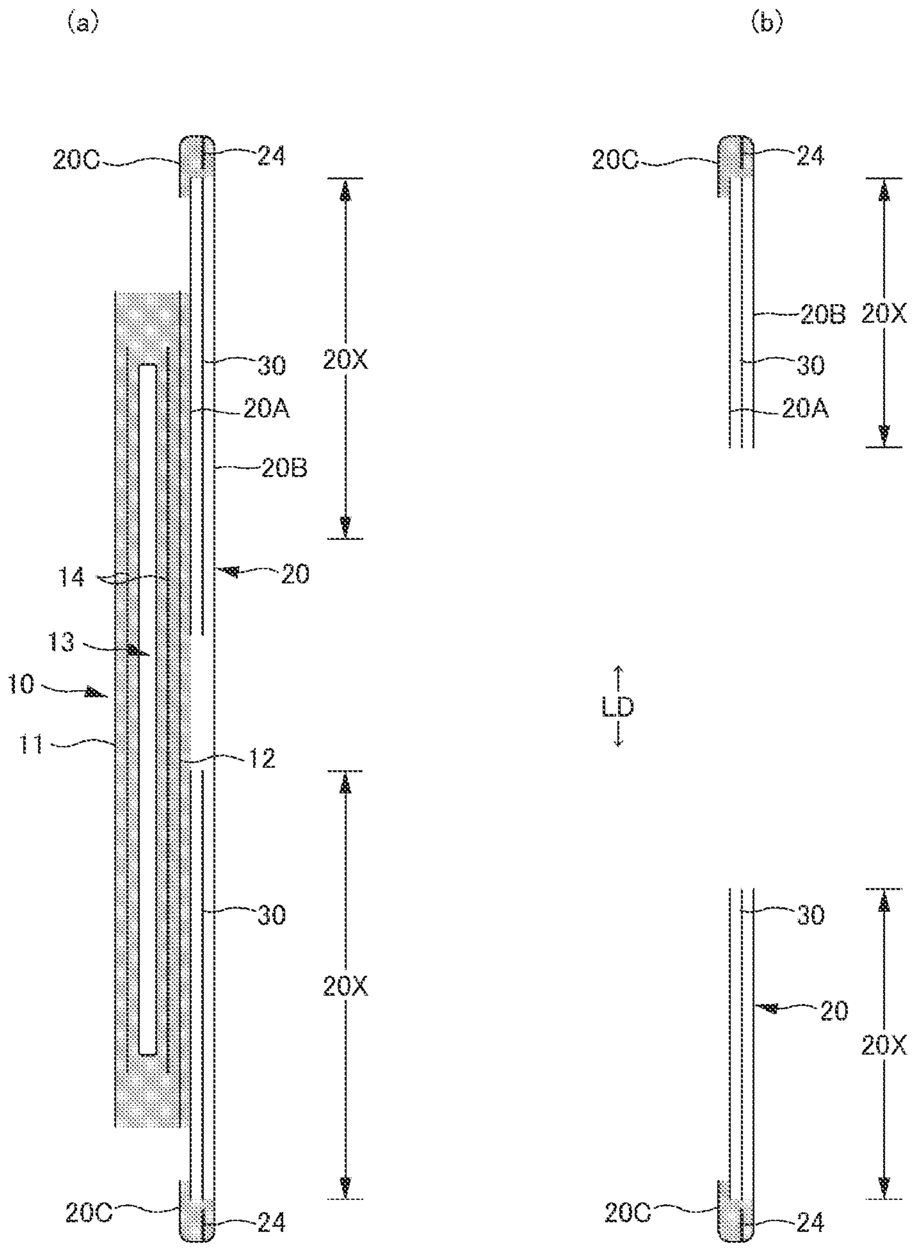

[FIG.9]
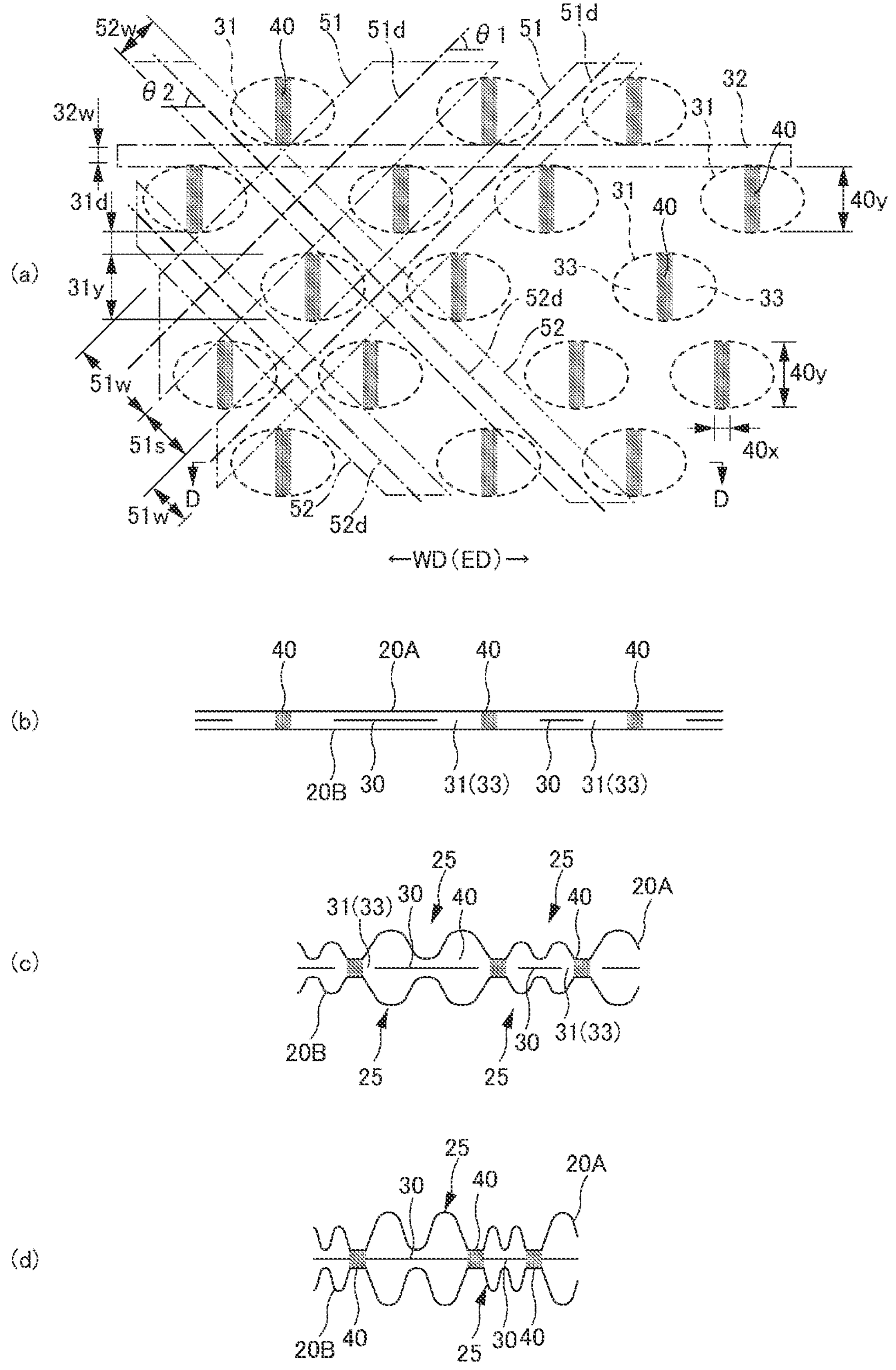

[FIG.10]
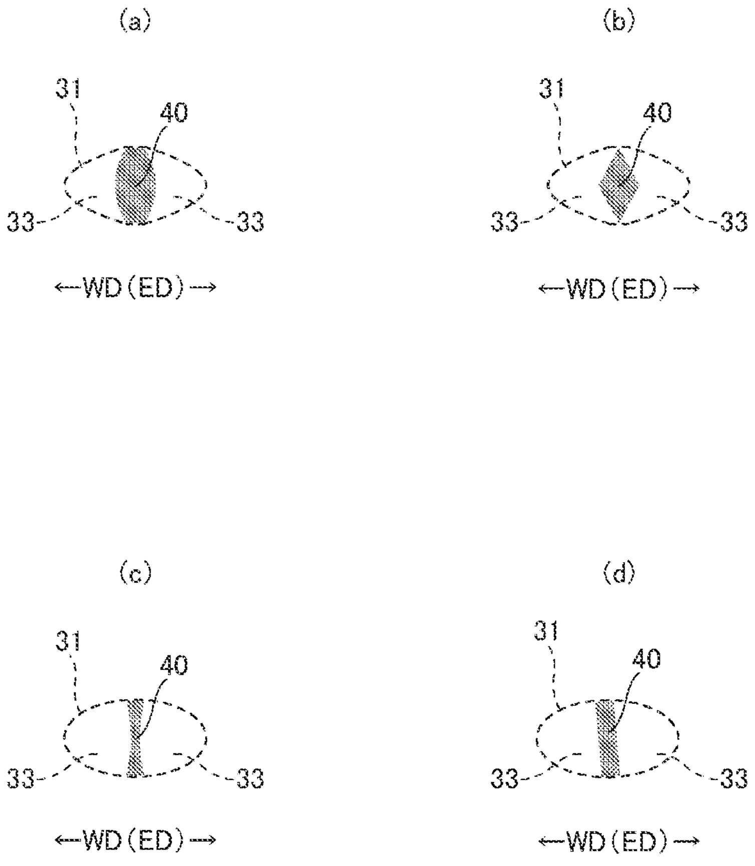

[FIG.11]
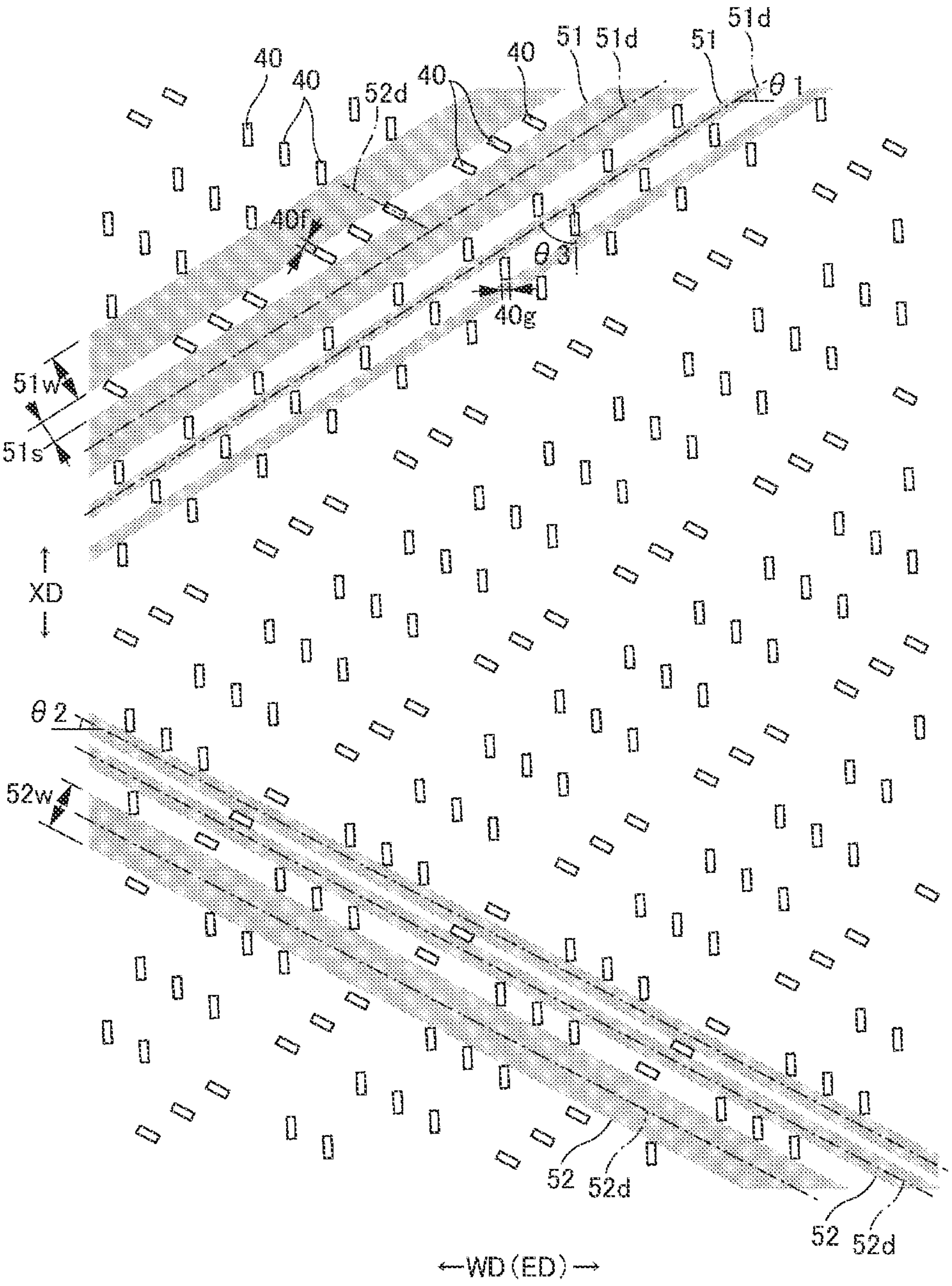

[FIG.12]
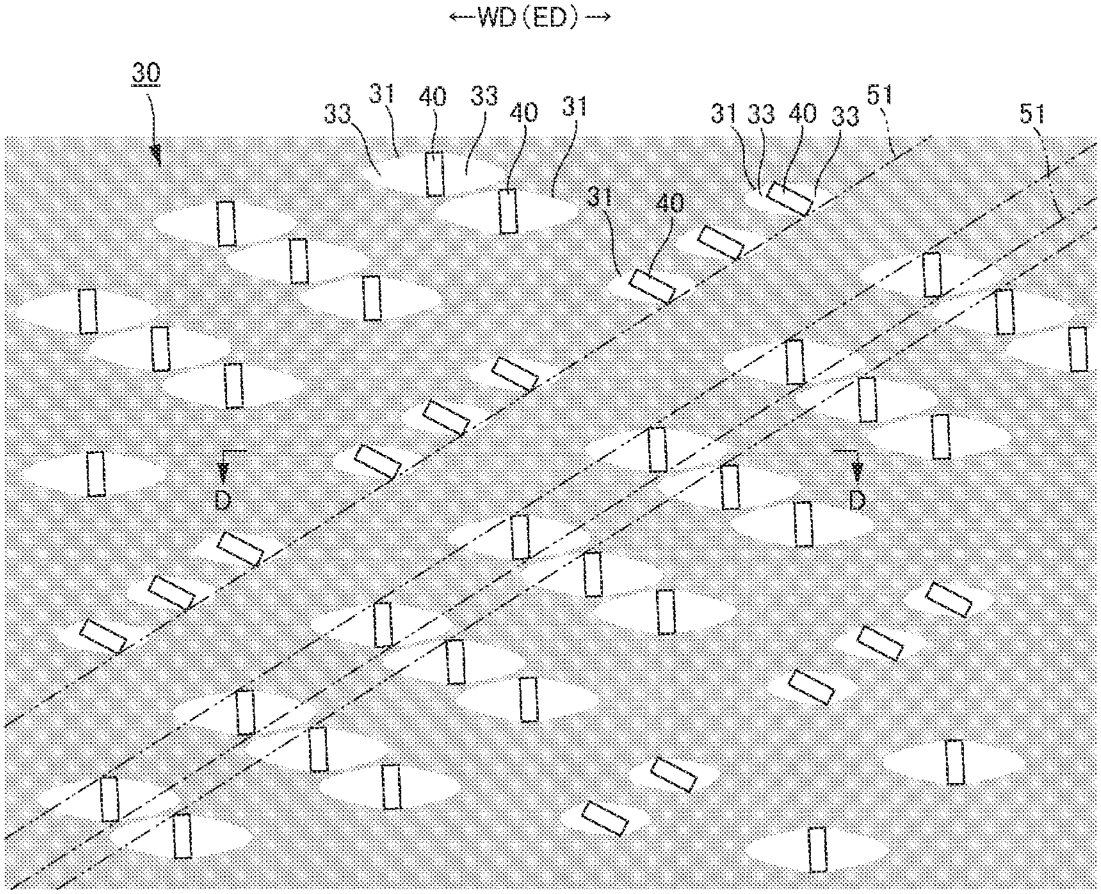

[FIG.13]
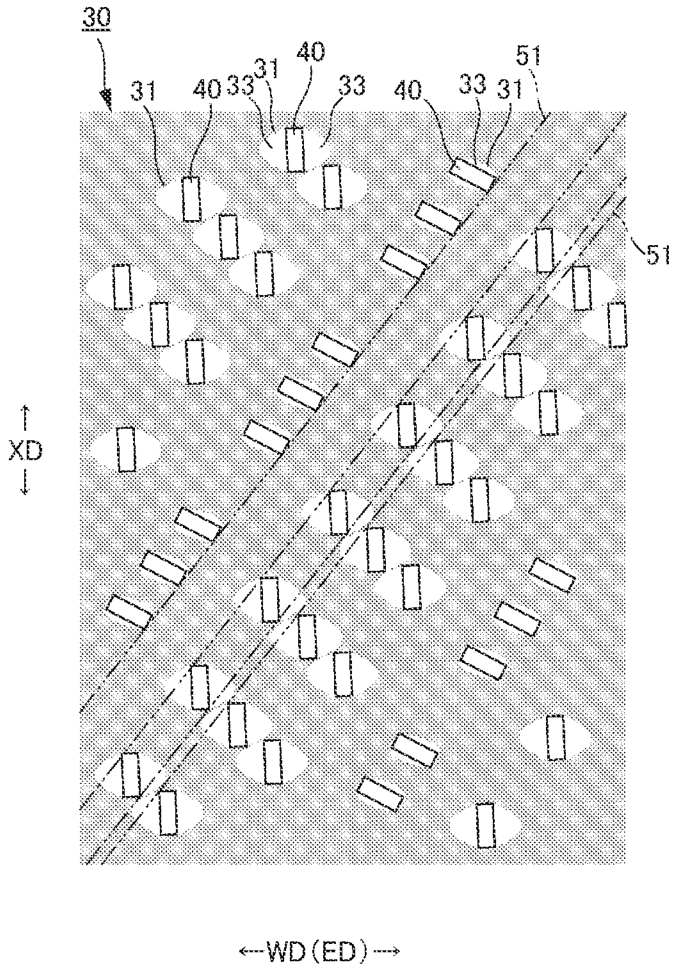

[FIG.14]
(a)
←WD(ED)→
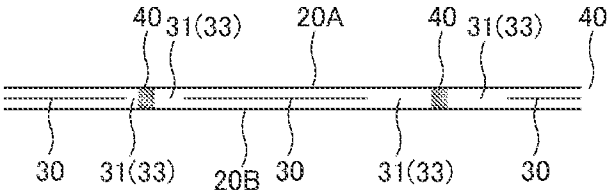
(b)
←WD(ED)→
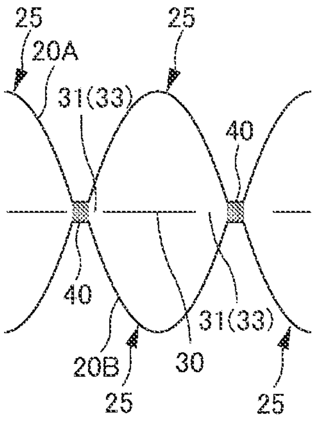

[FIG.15]
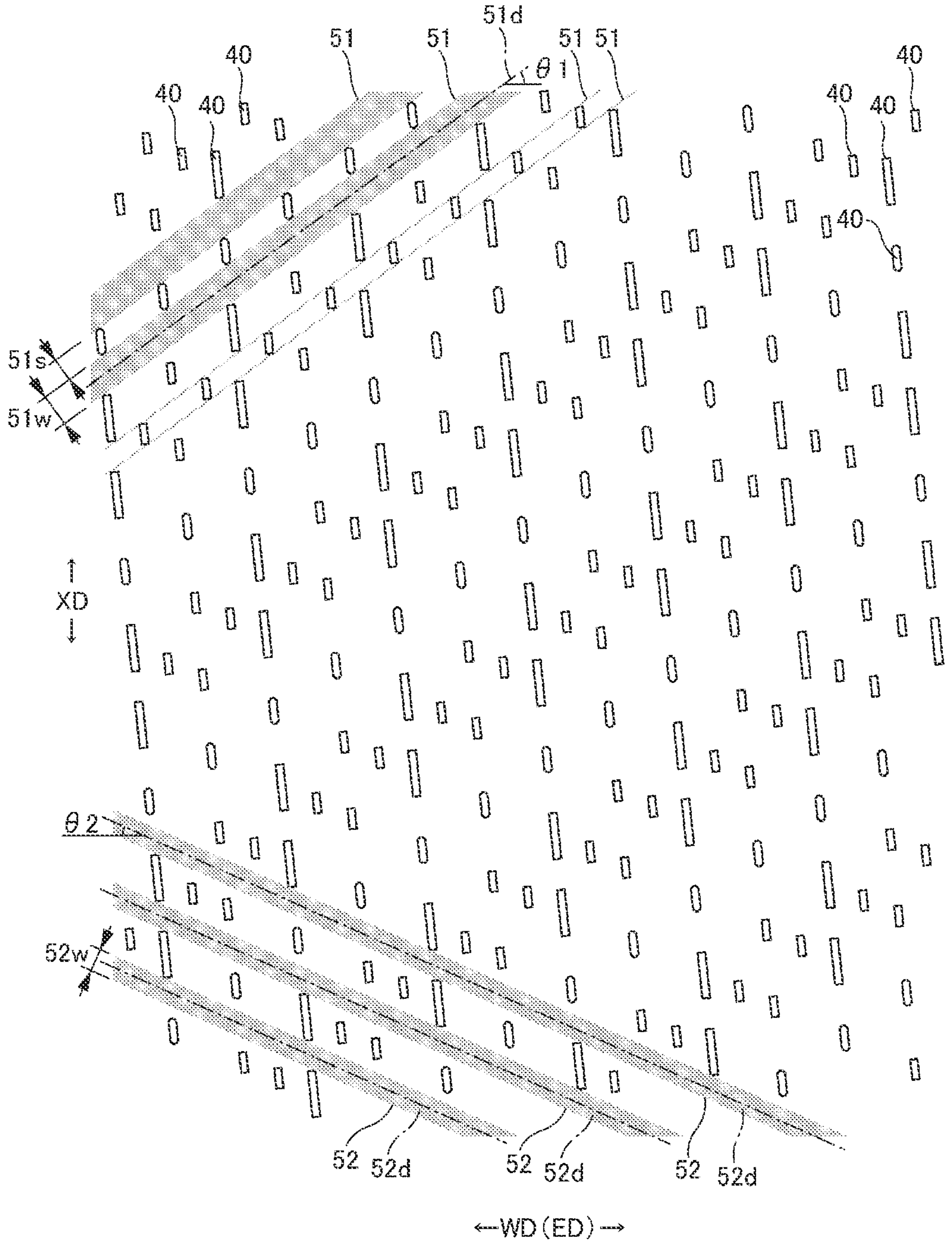

[FIG.16]
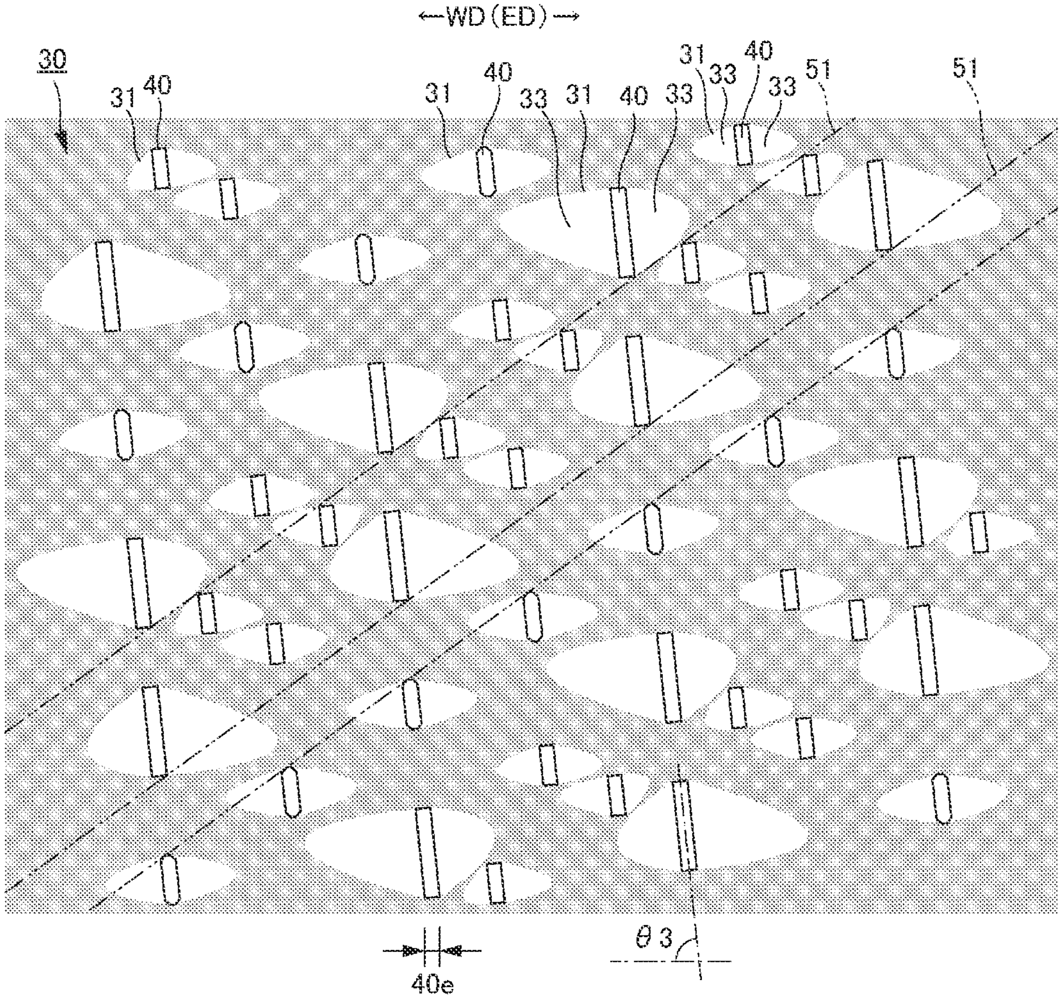

[FIG.17]
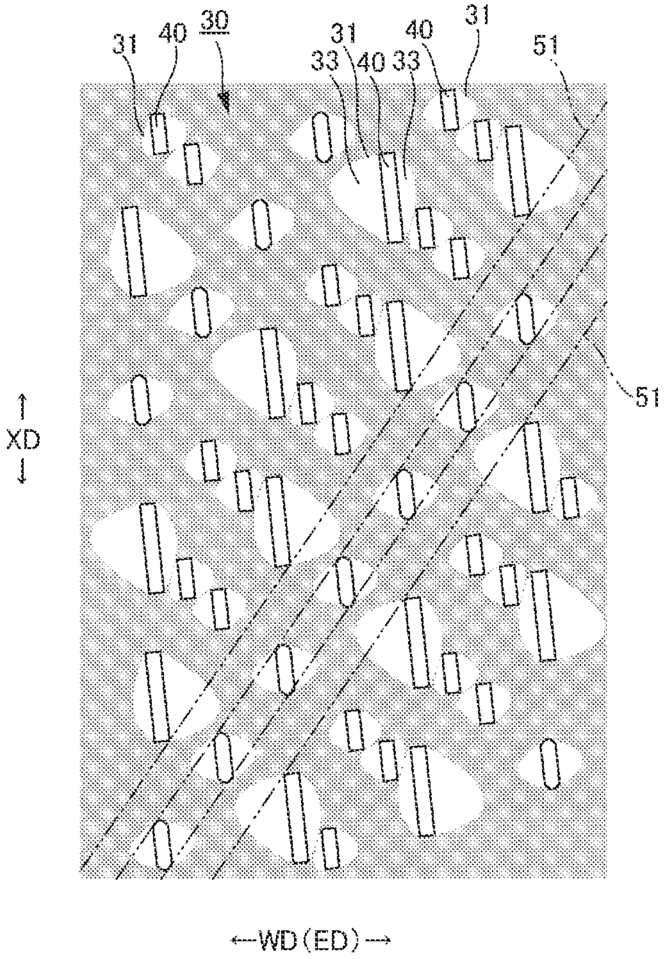

[FIG.18]
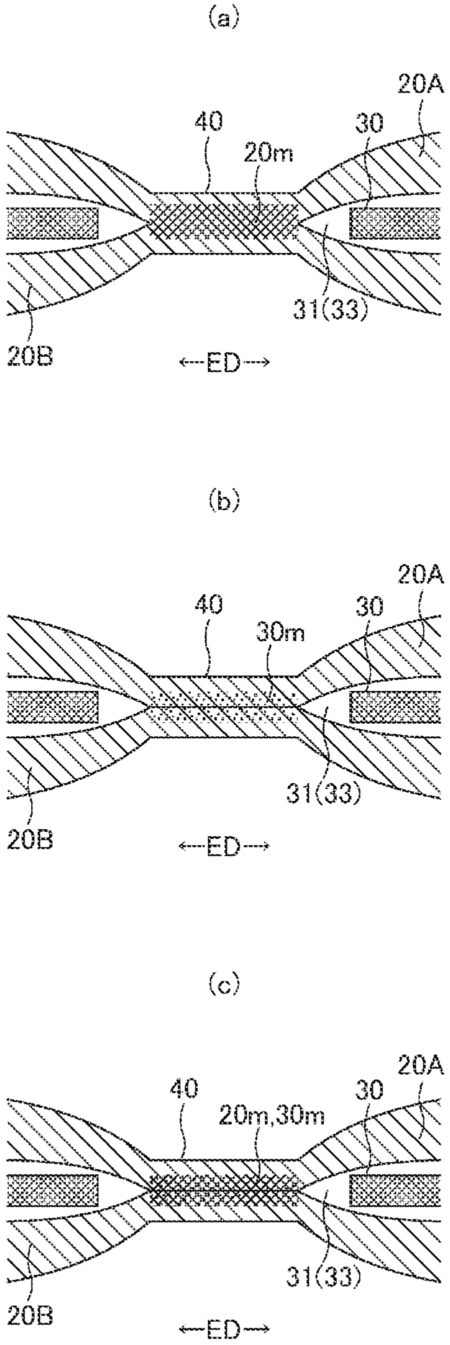

[FIG.19]
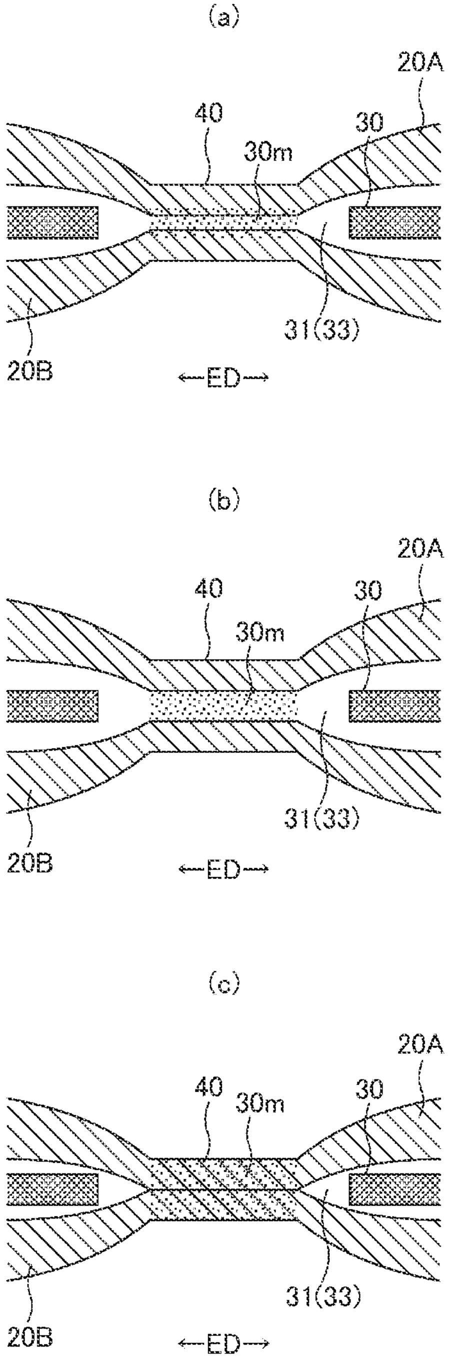

[FIG.20]
(a)
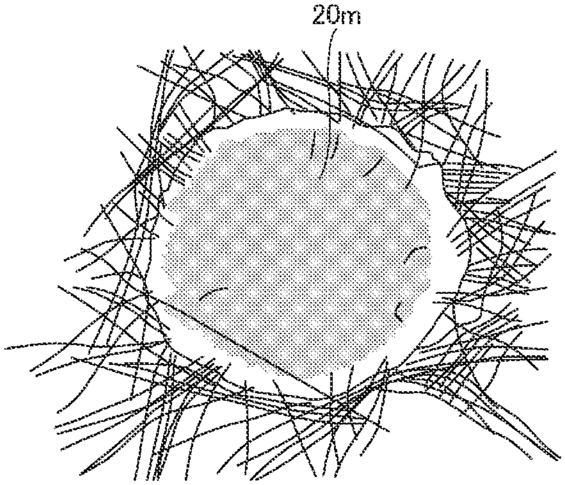
(b)
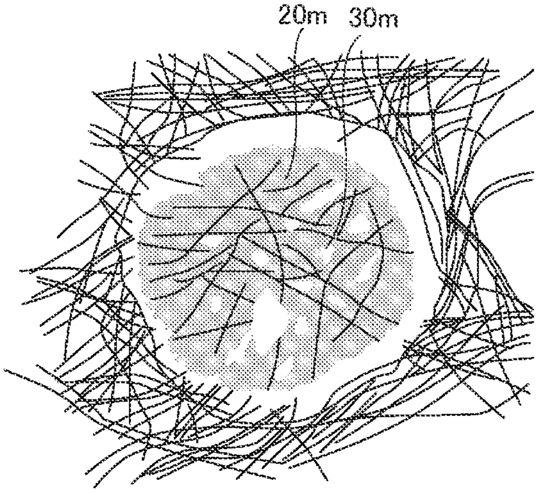

[FIG.21]
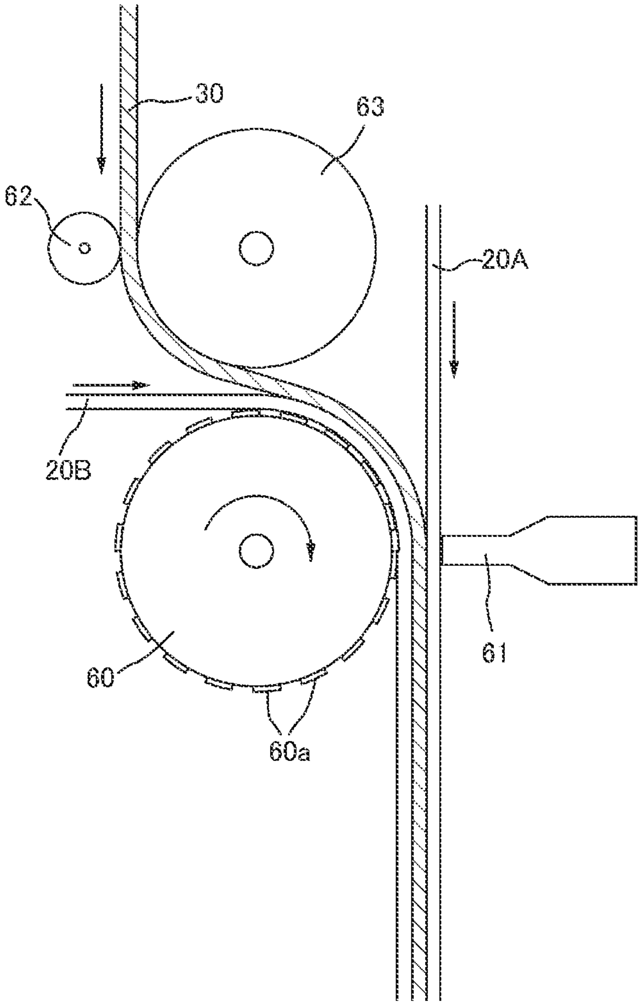

[FIG.22]
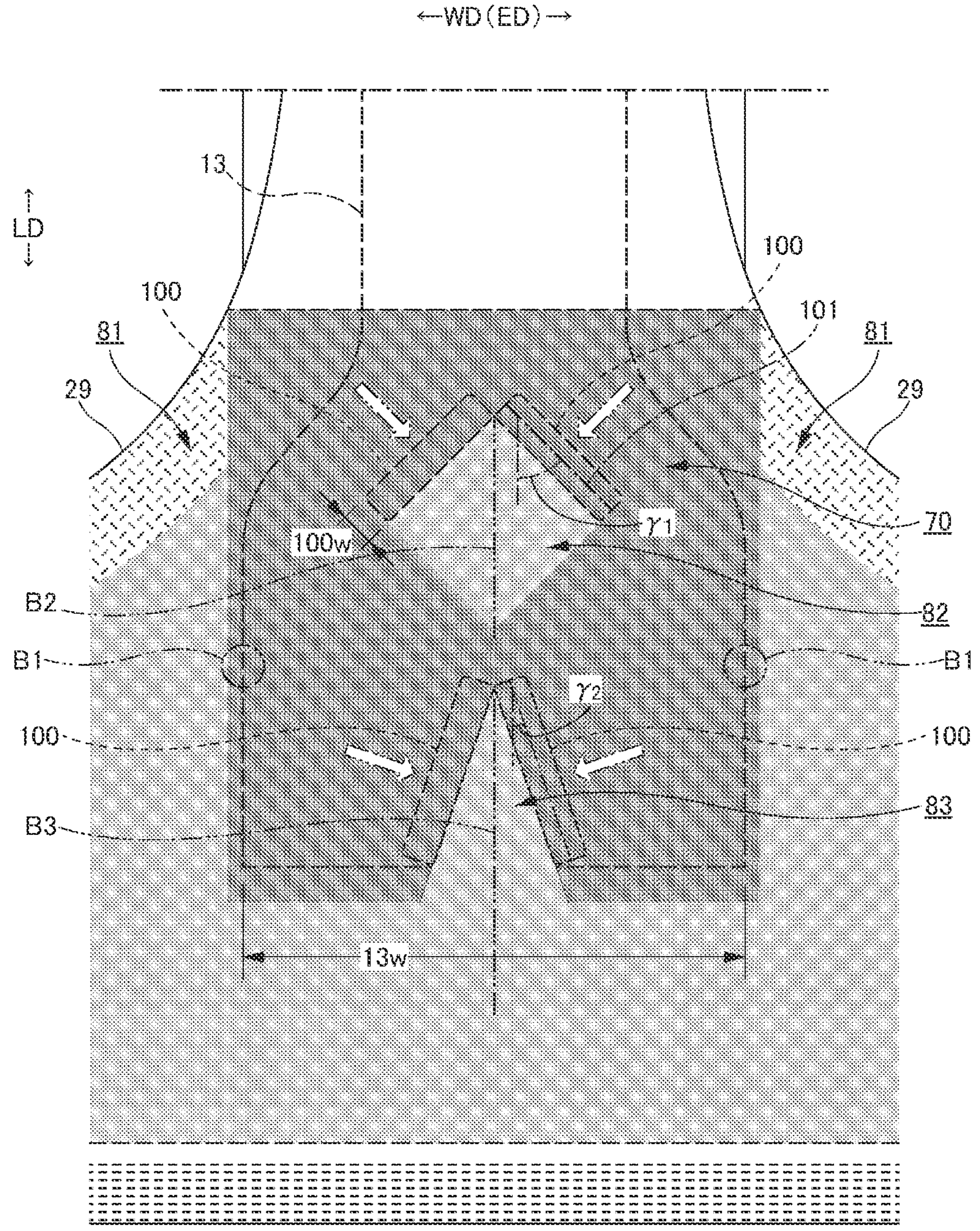

[FIG.23]
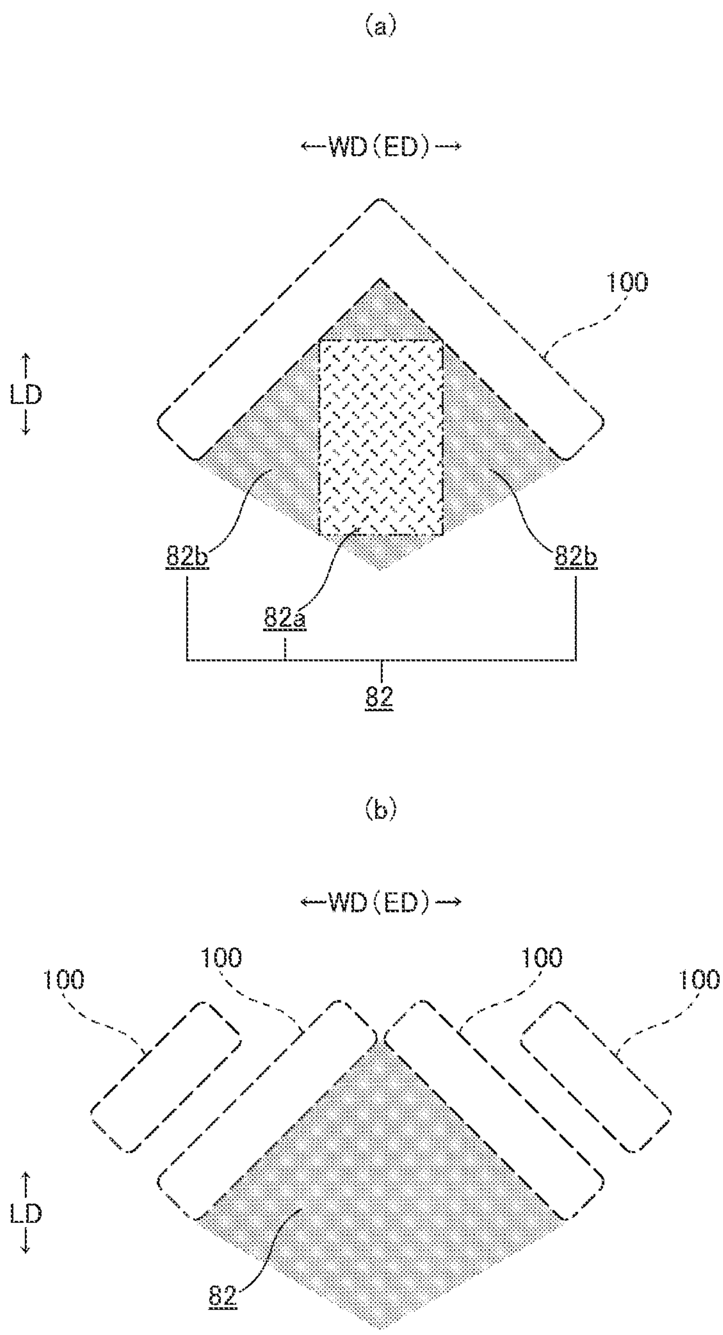

[FIG.24]
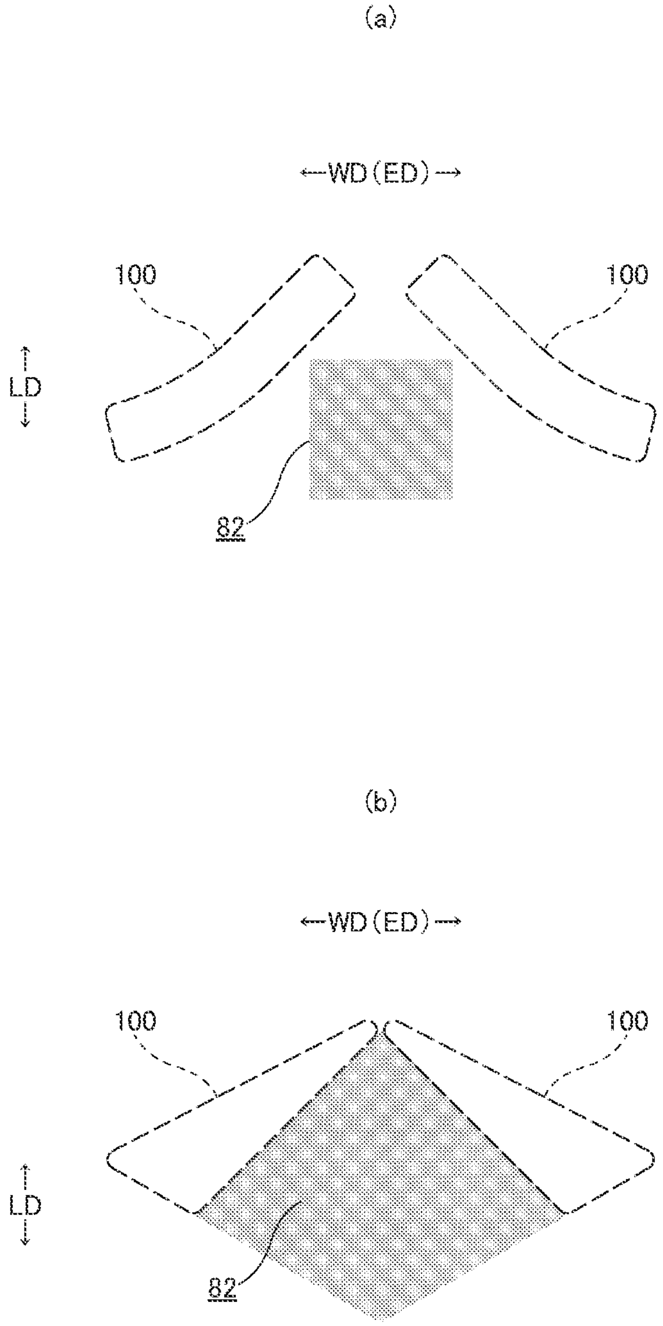

[FIG.25]
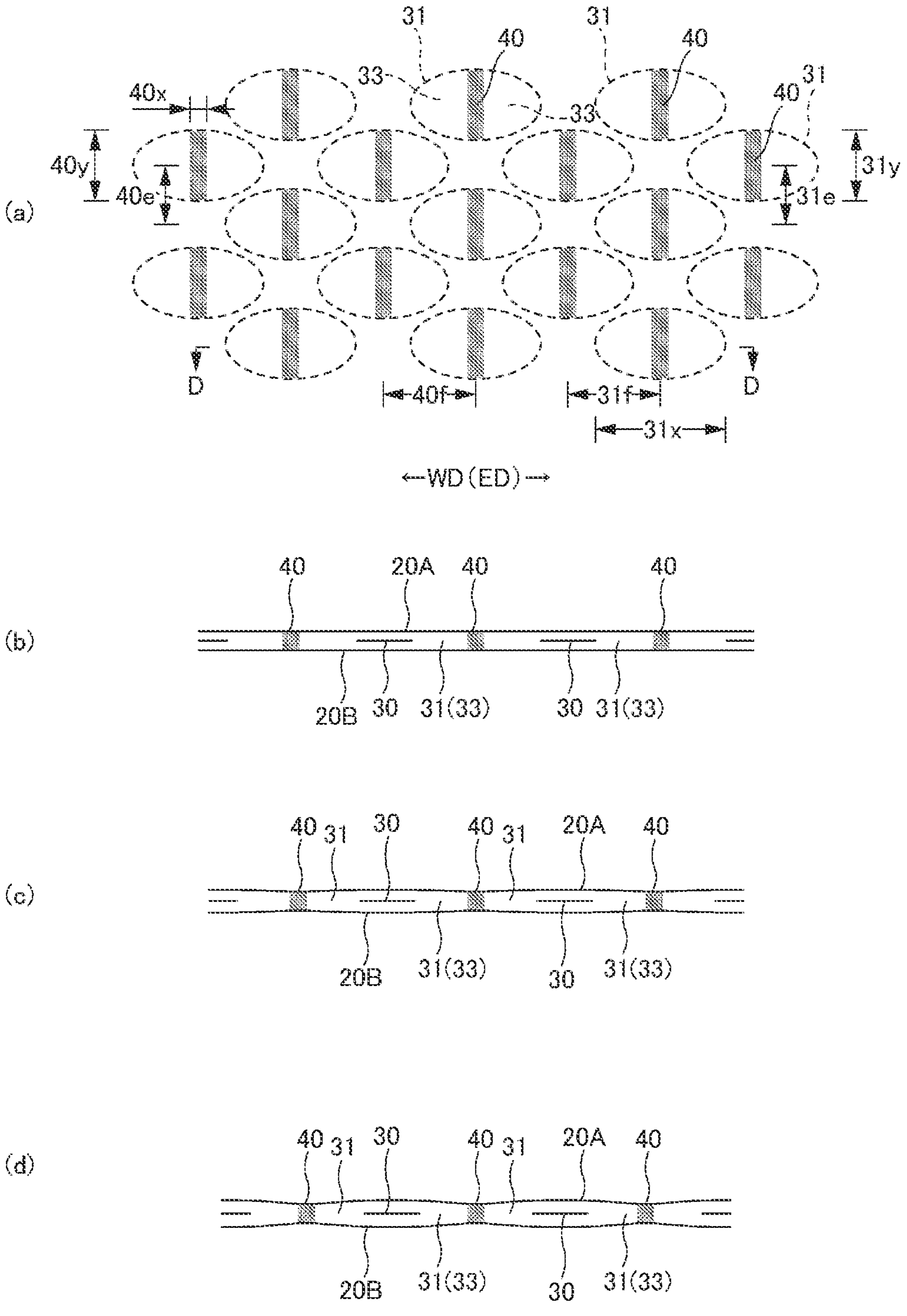

[FIG.26]
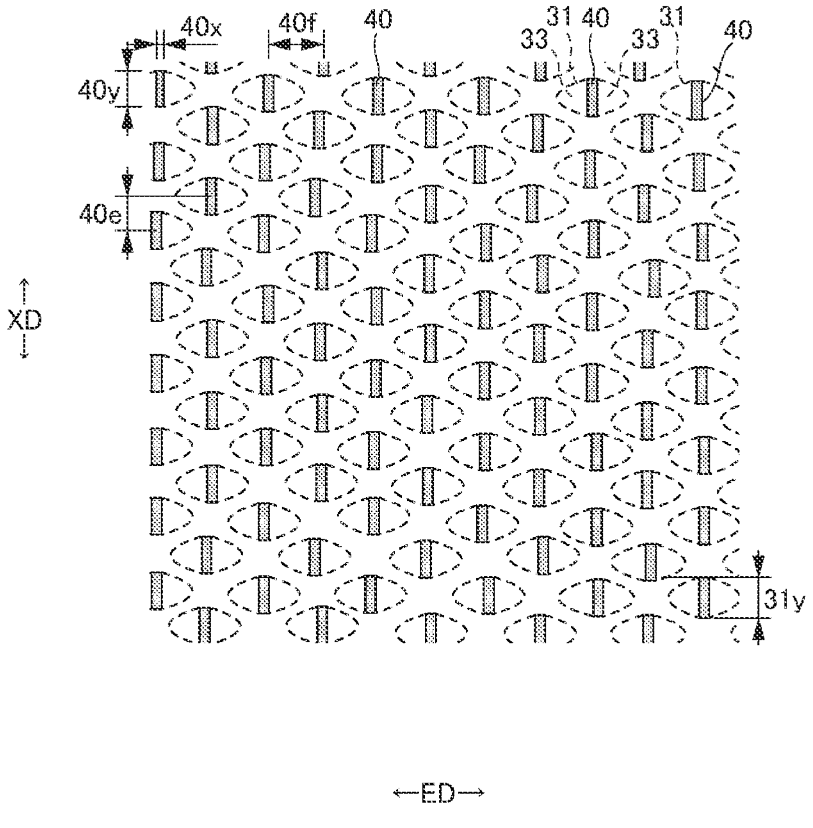

UNDERPANTS-TYPE DISPOSABLE WEARING ARTICLE

CROSS-REFERENCE TO RELATED APPLICATIONS

This application is the U.S. national stage application of International Application PCT/JP2022/014095, filed Mar. 24, 2022, which international application was published on Mar. 2, 2023, as International Publication WO 2023/026560 in the Japanese language. The International Application claims priority of Japanese Patent Application No. 2021-138050, filed Aug. 26, 2021. The international application and Japanese application are both incorporated herein by reference, in entirety.

TECHNICAL FIELD

The present invention relates to an underpants-type disposable wearing article excellent in fitting to an intergluteal cleft.

BACKGROUND ART

In a general underpants-type disposable wearing article, for ensuring fitting, rubber thread-shaped, net-shaped or film-shaped elastic members are attached to a lower torso region and the like in an outer member to form a stretchable region stretching and contracting between a natural length state where the stretchable region is contracted together with the elastic members to form pleats and a spread state where the stretchable region is stretched without forming the pleats (See Patent Literatures 1 to 3, for example).

Particularly, in each of underpants-type disposable wearing articles disclosed in Patent Literature 1 and Patent Literature 2, a stretchable region (intergluteal cleft stretchable region) is provided along a width direction in a portion facing an intergluteal cleft. Accordingly, this portion is more contracted in the width direction than portions on both sides thereof so as to bend and enter into the intergluteal cleft for fitting. Therefore, improved fitting not only to the intergluteal cleft but also to a whole of swollen gluteal can be preferably attained.

However, due to the improved fitting to the portion facing the intergluteal cleft, when a wearer walks, a lifting force, which is generated by backward movements of legs of the wearer, exerts alternately on both sides of the intergluteal cleft stretchable region in the width direction, so that unevenness, crack and twist of an absorber are likely to occur at both the sides of the intergluteal cleft stretchable region in the width direction. Such unevenness, crack and twist of the absorber produce undesirable results such as uncomfortable feeling to the wearer and unintentional deterioration of an absorption performance.

CITATION LIST

Patent Literature

Patent Literature 1: JP 2018-082853 A
Patent Literature 2: JP 2012-010905 A
Patent Literature 3: JP 2016-187386 A

SUMMARY OF INVENTION

Technical Problem

Therefore, a main object of the present invention is to suppress unevenness, crack and twist of an absorber, while improved fitting to an intergluteal cleft is to be attained.

Solution to Problem

An underpants-type disposable wearing article solving the above-mentioned problem is as follows.

First Aspect

An underpants-type disposable wearing article including:

an outer member forming at least a lower torso region of a front body part;

a lower torso region of a back body part and an absorber provided from the front body part to the back body part; and side seal portions in which both side portions of the front body part and both side portions of the back body part are bonded to each other, respectively, to form a waist opening and a left-and-right-pair of leg opening portions, wherein the back body part includes a pair of first portions, which face left and right gluteal peaks, respectively, and a second portion located in that range of a center line passing through a center of the back body part in a width direction, which faces an intergluteal cleft, an intergluteal cleft stretchable region is provided over both sides of the second portion in the width direction with an intergluteal cleft elastic member therein such that both side edges of the intergluteal cleft stretchable region are away from both imaginary straight lines to a center side thereof in the width direction, respectively, the imaginary straight lines passing through both the first portions along a front-back direction, respectively, the intergluteal cleft stretchable region stretches and contracts in the width direction between a natural length state where the intergluteal cleft stretchable region is contracted together with the intergluteal cleft elastic member, and a spread state where the intergluteal cleft stretchable region is stretched to be spread together with the intergluteal cleft elastic member, a maximum elongation in the width direction of the intergluteal cleft stretchable region is larger than a maximum elongation in the width direction of a region, which is adjacent to the intergluteal cleft stretchable region on both sides thereof in the width direction, the absorber extends backward beyond the first portions, and both side edges of the absorber extend, in the back body part, so as to pass through positions, which are away from both line segments to outer sides thereof in the width direction, respectively, the both line segments connecting the first portions and a front end of the second portion, respectively, and in the absorber, at both the sides of the intergluteal cleft stretchable region in the width direction, slots are formed to extend outwardly in the width direction toward a back side, respectively.

(Effect)

In the present underpants-type disposable wearing article provided with the intergluteal cleft stretchable region, improved fitting to the intergluteal cleft may be attained.

However, with only the intergluteal cleft stretchable region formed, as stated above, when a wearer walks, a lifting force, which is generated by backward movements of legs of the wearer, exerts alternately on both the sides of the intergluteal cleft stretchable region in the width direction, so that the unevenness, crack and twist of the absorber are likely to occur at both the sides of the intergluteal cleft stretchable region in the width direction.

On the contrary, in the absorber of the present underpants-type disposable wearing article, at both the sides of the intergluteal cleft stretchable region in the width direction, slots (elongated holes in a plan view penetrating the absorber in a thickness direction) are formed to extend outwardly in the width direction toward the back side, respectively. In this way, even when the lifting force exerts alternately on both the sides of the intergluteal cleft stretchable region in the width direction, the absorber deforms such that the widths of the slots are decreased (in a manner where the slots are closed), respectively, thus, the force can be absorbed. As a result, the unevenness, crack and twist of the absorber at both the sides of the intergluteal cleft stretchable region in the width direction can be suppressed, while the improved fitting to the intergluteal cleft can be attained by the intergluteal cleft stretchable region.

Second Aspect

The underpants-type disposable wearing article according to the first aspect, wherein acute intersecting angles between the front-back direction and directions along which the slots extend are 30 to 70 degrees, respectively.

(Effect)

The directions along which the slots extend can be determined as appropriate according to a shape of round-leg portions of the underpants-type disposable wearing article and arrangements of various kinds of elastic members, respectively, and in a normal case, the acute intersecting angles between the front-back direction and the directions along which the slots extend are preferably within a range of the present aspect, respectively.

Incidentally, the directions along which the slots extend refer to directions along which center lines of the slots extend, respectively. Further, in a case where the directions along which the slots extend are curved like circular arcs, the directions along which the slots extend refer to directions along which tangential lines of the center lines of the slots extend, respectively.

Third Aspect

The underpants-type disposable wearing article according to the first or second aspect, wherein, those portions of both the side edges of the intergluteal cleft stretchable region, which correspond to both the slots at least locating in the width direction, respectively, extend in parallel with directions along which both the slots extend, respectively.

(Effect)

It is preferable that there is a positional relation between the side edges of the intergluteal cleft stretchable region and the directions along which the slots extend as in the present aspect, because when the lifting force, which is generated by the backward movements of the legs, exerts, the absorber may be deformed easily so as to, in particular, decrease the widths of the slots.

Fourth Aspect

The underpants-type disposable wearing article according to any one of the first to third aspects, wherein the slots are adjacent to the intergluteal cleft stretchable region.

(Effect)

It is preferable that there is a positional relation between the side edges of the intergluteal cleft stretchable region and the directions along which the slots extend as in the present aspect, because when the lifting force, which is generated by the backward movements of the legs, exerts, the force may be applied easily, in particular, to the slots of the absorber. As an example, intervals between edges of the slots on the center side in the width direction and the side edges of the intergluteal cleft stretchable region are preferably about 20 to 50 mm, respectively.

Fifth Aspect

The underpants-type disposable wearing article according to any one of the first to fourth aspects, wherein the intergluteal cleft stretchable region includes a first sheet layer, a second sheet layer and an elastic sheet disposed therebetween as the intergluteal cleft elastic member, and the first sheet layer and the second sheet layer are bonded directly or indirectly at a large number of joined portions arranged at intervals, at least in a middle part of the intergluteal cleft stretchable region in the front-back direction, an area ratio of the joined portions decreases stepwise or continuously from both side edges of the middle part toward the center thereof in the width direction, respectively.

(Effect)

In an elastic sheet stretchable structure, a percentage of contraction becomes higher as an area ratio of the joined portions is stepwise or continuously decreased. Thus, in the present aspect, in the intergluteal cleft stretchable region, the percentage of contraction becomes higher from both the side edges of the middle part toward the center thereof in the width direction. The intergluteal cleft stretchable region of the present aspect therefore becomes excellent particularly in the fitting to the intergluteal cleft.

Sixth Aspect

The underpants-type disposable wearing article according to any one of the first to fifth aspects, wherein the back body part has a non-stretchable region, which is adjacent to the intergluteal cleft stretchable region at both sides thereof in the width direction and located at the center side of both the side edges of the absorber in the width direction, and a side stretchable region, which is adjacent to the non-stretchable region at both sides thereof in the width direction and extended to outer sides of both the side edges of the absorber in the width direction, a region, which is provided from a part of the side stretchable region on one side, through a part of the non-stretchable region on one side, the intergluteal cleft stretchable region, and a part of the non-stretchable region on the other side, to a part of the side stretchable region on the other side includes a first sheet layer, a second sheet layer and an elastic sheet forming the intergluteal cleft elastic member and being disposed therebetween, and the first sheet layer and the second sheet layer are bonded directly or indirectly at a large number of joined portions arranged at intervals, a maximum elongation in the width direction of the non-stretchable region is less than 120%, a maximum elongation of the intergluteal cleft stretchable region is 1.5 to 3 times the maximum elongation in the width direction of the non-stretchable region, a maximum elongation of the side stretchable region is 2 to 5 times the maximum elongation in the width direction of the non-stretchable region, the slots are provided only in the non-stretchable region.

(Effect)

When the elastic sheet stretchable structure is adopted, if the non-stretchable region having the maximum elongation of less than 120% in the width direction is adjacent to the intergluteal cleft stretchable region at both the sides thereof in the width direction and the slots are arranged only in the non-stretchable region, the widths of the slots become unlikely to be decreased in a situation where the lifting force, which is generated by the backward movements of the legs, does not exert. In this case, the widths of the slots do not need to be increased to an excessive degree in order to prepare for a situation where the lifting force exerts, and thereby decrease of an absorption amount may be prevented.

Seventh Aspect

The underpants-type disposable wearing article according to any one of the first to six aspects, wherein the back body part includes a third portion, which is a part of the center line passing through the center of the back body part in the width direction and located in a range facing a sacrum, a sacrum stretchable region is provided over both sides of the third portion in the width direction with a sacrum elastic member therein such that both side edges of the sacrum stretchable region are away from both the imaginary straight lines to the center side thereof in the width direction, respectively, the imaginary straight lines passing through both the first portions along the front-back direction, respectively, the sacrum stretchable region stretches and contracts in the width direction between a natural length state where the sacrum stretchable region is contracted together with the sacrum elastic member, and a spread state where the sacrum stretchable region is stretched to be spread together with the sacrum elastic member, a maximum elongation in the width direction of the sacrum stretchable region is larger than a maximum elongation in the width direction of a region, which is adjacent to the sacrum stretchable region on both sides thereof in the width direction, the absorber extends backward beyond the front end of the third portion, and both the side edges of the absorber are away from both side edges of the third portion to outer sides thereof in the width direction, respectively, and in the absorber, at both the sides of the sacrum stretchable region in the width direction, slots are formed to extend outwardly in the width direction toward the back side, respectively.

(Effect)

In the present underpants-type disposable wearing article provided with the sacrum stretchable region, improved fitting to a dent formed on a body surface at the sacrum may be attained. However, with only the sacrum stretchable region formed, when the wearer walks or when the wearer twists an upper part of the body while sitting, a lifting force, which is generated by backward movements of legs, exerts alternately on both the sides of the sacrum stretchable region in the width direction, so that unevenness, crack and twist of the absorber are likely to occur at both the sides of the sacrum stretchable region in the width direction.

On the contrary, in the absorber of the present underpants-type disposable wearing article, at both the sides of the sacrum stretchable region in the width direction, the slots (elongated holes in a plan view penetrating the absorber in the thickness direction) are formed to extend outwardly in the width direction toward the back side, respectively. In this way, even when the lifting force exerts alternately on both the sides of the sacrum stretchable region in the width direction, the absorber deforms such that the widths of the slots are decreased (in a manner where the slots are closed), thus, the force can be absorbed. As a result, the unevenness, crack and twist of the absorber at both the sides of the sacrum stretchable region in the width direction can be suppressed, while the improved fitting to the dent formed on the body surface at the sacrum can be attained by the sacrum stretchable region.

Eighth Aspect

The underpants-type disposable wearing article according to the seventh aspect, wherein acute inclination angles between the front-back direction and directions along which the slots provided at both the sides of the sacrum stretchable region in the width direction extend are 0.3 to 0.8 times the acute intersecting angles between the front-back direction and the directions along which the slots provided at both the sides of the intergluteal cleft stretchable region in the width direction extend, respectively.

(Effect)

It is preferable that the angles are changed as stated in the present aspect, because the slots at respective positions become able to perform their own functions sufficiently.

Advantageous Effects of Invention

The present invention provides advantages such as an ability to suppress unevenness, crack and twist of an absorber, while improved fitting to an intergluteal cleft is to be attained.

BRIEF DESCRIPTION OF DRAWINGS

FIG. 1 is a plan view (internal surface side) of an underpants-type disposable diaper in a spread state.

FIG. 2 is a plan view (external surface side) of the underpants-type disposable diaper in the spread state.

FIG. 3 is a plan view illustrating only a main part of the underpants-type disposable diaper in the spread state.

FIG. 4(*a*) is a cross-sectional view taken along C-C line of FIG. 1, and FIG. 4(*b*) is a cross-sectional view taken along E-E line of FIG. 1.

FIG. 5 is a cross-sectional view taken along A-A line of FIG. 1.

FIG. 6 is a cross-sectional view taken along B-B line of FIG. 1.

FIG. 7 is a plan view (external surface side) of an underpants-type disposable diaper in a spread state.

FIG. 8(*a*) is a cross-sectional view taken along C-C line of FIG. 7, and FIG. 8(*b*) is a cross-sectional view taken along E-E line of FIG. 7.

FIG. 9(*a*) is a plan view of a main part of a stretchable region, FIG. 9(*b*) is a cross-sectional view taken along D-D line of FIG. 9(*a*), FIG. 9(*c*) is a cross-sectional view in a worn state, and FIG. 9(*d*) is a cross-sectional view in a natural length state.

FIG. 10 is a plan view illustrating various shapes of joined portions.

FIG. 11 is a plan view of the stretchable region in the spread state.

FIG. 12 is an enlarged plan view illustrating a main part of the stretchable region in the spread state.

FIG. 13 is an enlarged plan view illustrating a main part of the stretchable region in the natural length state.

FIG. 14(*a*) is a cross-sectional view taken along D-D line of FIG. 12 and FIG. 14(*b*) is a cross-sectional view in the natural length state.

FIG. 15 is a plan view of the stretchable region in the spread state.

FIG. 16 is an enlarged plan view illustrating the main part of the stretchable region in the spread state.

FIG. 17 is an enlarged plan view illustrating the main part of the stretchable region in the natural length state.

FIG. 18 is a cross-sectional view schematically illustrating a cross section of a main part of an outer member stretched to some extent.

FIG. 19 is a cross-sectional view schematically illustrating a cross section of a main part of an outer member stretched to some extent.

FIG. 20(*a*) is a trace view of a plane photograph of a joined portion formed in a first welding mode, and FIG. 20(*b*) is a trace view of a plane photograph of a joined portion formed in a third welding mode.

FIG. 21 is a schematic view of an ultrasonic sealing device.

FIG. 22 is an enlarged plan view illustrating a main part of the stretchable region in the natural length state.

FIG. 23 is an enlarged plan view illustrating the main part of the stretchable region in the spread state.

FIG. 24 is a cross-sectional view schematically illustrating an elastic sheet stretchable structure.

FIG. 25(*a*) is a plan view of a main part of a non-stretchable region, FIG. 25(*b*) is a cross-sectional view taken along D-D line of FIG. 25(*a*), FIG. 25(*c*) is a cross-sectional view in a worn state, and FIG. 25(*d*) is a cross-sectional view in a natural length state.

FIG. 26 is a plan view of the main part of the non-stretchable region.

DESCRIPTION OF EMBODIMENTS

Hereinafter, a detailed description will be given of an underpants-type disposable diaper as a typical example of an underpants-type disposable wearing article, referring to accompanying drawings. Incidentally, each of dotted pattern regions in the drawings indicates an adhesive as a bonding means that bonds respective components located on a top side and an underside thereof. The adhesive may be applied by solid, bead, curtain, summit, or spiral coating of a hot melt adhesive, or pattern coating (transfer of the hot melt adhesive in a letterpress method). Further, instead of or together with the above methods, the elastic member can be fixed by applying the hot melt adhesive to an outer peripheral surface of an elastic member by means of comb gun or sure wrap application or the like. Examples of the hot melt adhesive include EVA-based, pressure sensitive adhesion rubber-based (elastomer-based), polyolefin-based, and polyester/polyamide-based adhesives, and can be used without any particular limitation. As bonding means that bonds respective components, it is possible to use means by material welding such as heat sealing or ultrasonic sealing.

Further, as a nonwoven fabric in the following description, a known nonwoven fabric can be appropriately used according to a site or a purpose. Examples of a constituent fiber of the nonwoven fabric include, but are not limited to, a synthetic fiber such as a polyolefin-based fiber including polyethylene and polypropylene, a polyester-based fiber, or a polyamide-based fiber (including a composite fiber such as core-sheath in addition to a single component fiber), a regenerated fiber such as rayon or cupra, and a natural fiber such as cotton. These fibers can be mixed and used. In order to enhance flexibility of the nonwoven fabric, it is preferable to use a crimped fiber as the constituent fiber. In addition, the constituent fiber of the nonwoven fabric may be a hydrophilic fiber (including a fiber that has become hydrophilic by a hydrophilizing agent), a hydrophobic fiber, or a water-repellent fiber (including a fiber that has become water-repellent by a water repellent agent). In addition, the nonwoven fabric is generally classified into a short fiber nonwoven fabric, a long fiber nonwoven fabric, a spunbond nonwoven fabric, a meltblown nonwoven fabric, a spunlace nonwoven fabric, a thermal bond (air-through) nonwoven fabric, a needle punch nonwoven fabric, a point bond nonwoven fabric, a laminated nonwoven fabric (an SMS nonwoven fabric, an SMMS nonwoven fabric, or the like in each of which different nonwoven fabric layers are laminated and a meltblown layer is sandwiched between spunbond layers, in addition to SSS nonwoven fabric in which same or similar nonwoven fabric layers are laminated), and the like depending on a fiber length, a sheet forming method, a fiber bonding method, and a stacked structure, and any of these nonwoven fabrics can be used. The laminated nonwoven fabric is manufactured as one unit including all layers integrally, and refers to a fabric processed by bonding fibers across the all layers. However, the laminated nonwoven fabric does not include a fabric formed by sticking, with a bonding means such as a hot melt adhesive, a plurality of nonwoven fabrics which have been manufactured separately.

FIG. 1 to FIG. 6 show an underpants-type disposable diaper including a front body part F covering a front side of a wearer and a back body part B covering a back side of the wearer. A reference character LD (longitudinal direction) denotes a front-back direction, and a reference character WD denotes a width direction. The underpants-type disposable diaper (hereinafter also simply referred to as a diaper) in the illustrated example includes an outer member 20 forming at least a lower torso region T and an inner member 10 fixed to the outer member 20, and the inner member 10 is provided with an absorber 13 therein. In manufacturing, after an underside surface of the inner member 10 is bonded to an internal surface (upper surface) of the outer member 20 by bonding means such as a hotmelt adhesive, the inner member 10 and the outer member 20 are folded back at a center in the front-back direction LD (longitudinal direction) corresponding to a boundary between the front body part F and the back body part B, and both side portions thereof are bonded to each other by thermal welding or the hotmelt adhesive to form side seal portions 21, thereby obtaining the underpants-type disposable diaper in which a waist opening and a left-and-right-pair of leg opening portions are formed.

In particular, the back body part B in the illustrated example includes, as shown in enlarged view of FIG. 22, a pair of first portions B1, which face a left gluteal peak (top of a left gluteal swell) and a right gluteal peak (top of a right gluteal swell), respectively, and a second portion B2 located in that range of a center line passing through a center of the back body part in a width direction WD, which faces an intergluteal cleft. In addition, the back body part B includes also a third portion B3, which is a part of the center line passing through the center of the back body part in the width direction WD and located in a range facing a sacrum.

Positions of the first portion B1, the second portion B2 and the third portion B3 can be determined as appropriate according to dimensions, designs and the like of a product. As an example, in a spread state of the product from which the side seal portions 21 are removed by cutting along edges thereof on a center side, respectively, assuming that a position of an edge of the waist opening of the front body part F corresponds to 0% and a position of an edge of the waist opening of the back body part B corresponds to 100%, the first portions B1 may be located in a range of 50 to 80%. In addition, in a spread state of the product (in a state in which the product is stretched to a maximum elongation in the width direction WD by pulling the product from both side ends thereof while one of the side seal portions 21 and the other of the side seal portions 21 are pinched, respectively), assuming that a side edge of one of the side seal portions 21 of the back body part B corresponds to 0% and a side edge of the other of the side seal portions 21 of the back body part B corresponds to 100%, one of the first portions B1 may be located in a range of 20 to 40% and the other of the first portions B1 may be located in a range of 60 to 80%, respectively. The positions of the first portions B1 in the width direction WD may be on both side edges of the absorber 13, respectively.

In addition, in the spread state of the product from which the side seal portions 21 are removed by cutting along the edges thereof on the center side, respectively, assuming that the position of the edge of the waist opening of the front body part F corresponds to 0% and the position of the edge of the waist opening of the back body part B corresponds to 100%, the second portion B2 may refer to a portion extending from a position in a range of 50 to 70% to a position in a range of 60 to 80%. Further, in the spread state of the product from which the side seal portions are removed by cutting along the edges thereof on the center side, respectively, assuming that the position of the edge of the waist opening of the front body part F corresponds to 0% and the position of the edge of the waist opening of the back body part B corresponds to 100%, the third portion B3 may refer to a portion extending from a position in a range of 60 to 80% to a position in a range of 70 to 90%.

(Example of Inner Member)

As illustrated in FIG. 4 to FIG. 6, the inner member 10 has a structure in which the absorber 13 is interposed between a liquid pervious top sheet 11 and a liquid impervious sheet 12 made of polyethylene, etc. and absorbs and holds excretion fluid passing through the top sheet 11. A planar shape of the inner member 10 is not particularly limited. However, a substantially rectangular shape is generally adopted as shown in FIG. 1.

As the top sheet 11 that covers a top side (skin contact side) of the absorber 13, a perforated or non-perforated nonwoven fabric, a porous plastic sheet, etc. is preferably used.

As the liquid impervious sheet 12 covering an underside (non-skin contact side) of the absorber 13, a liquid impervious plastic sheet such as polyethylene or polypropylene may be used. In particular, a sheet having a moisture penetration property may be preferably used from a viewpoint of preventing stuffiness. Examples thereof include a microporous sheet obtained by melt-kneading an inorganic filler and a polyolefin resin such as polyethylene or polypropylene, molding the melt-kneaded mixture into a sheet, and then stretching the sheet in one or two axial directions.

As the absorber 13, it is possible to use a known one, which is based on, for example, a pulp fiber stack, an assembly of filaments of cellulose acetate, etc., or a nonwoven fabric and which has superabsorbent polymer particles mixed therewith or fixed thereto, or the like as necessary. To hold the shape, to prevent the superabsorbent polymer particles from escaping from the absorber 13, and for other purposes, the absorber 13 can be wrapped in a wrapping sheet 14 having a liquid pervious and liquid retaining property such as crepe paper as necessary.

The absorber 13 is provided from the front body part F to the back body part B. In particular, it is preferable that the absorber 13 extends backward beyond the pair of first portions B1, which face the left and right gluteal peaks, respectively, and both the side edges of the absorber extend, in the back body part B, so as to pass through positions, which are away from both line segments to outer sides thereof in the width direction WD, provided that the both line segments connect the first portions B1 and a front end of the second portion B2 (located in that range of the center line passing through the center of the back body part in the width direction WD, which faces the intergluteal cleft), respectively. In addition, it is preferable that the absorber 13 extends backward beyond the front end of the third portion B3 facing the sacrum, and both the side edges of the absorber 13 are away from both side edges of the third portion B3 to outer sides thereof in the width direction WD, respectively.

The absorber 13 is preferably formed into a substantially hourglass shape having a narrower portion 13N narrower than both front and back sides at a crotch portion. However, it may have another shape such as a rectangular shape. A size of the narrower portion 13N can be determined as appropriate. A length of the narrower portion 13N in the front-back direction can be set to about 20 to 50% of a maximum length of the diaper, and a width of a narrowest portion thereof can be set to about 40 to 60% of a maximum width 13*w* of the absorber 13. In the case of having such a narrower portion 13N, when the planar shape of the inner member 10 is substantially rectangular, non-absorber side portions 17 not having the absorber 13 are formed at a portion corresponding to the narrower portion 13N of the absorber 13 in the inner member 10.

In the illustrated embodiment, the liquid impervious sheet 12 is folded back to the underside together with the top sheet 11 on both sides in the width direction WD of the absorber 13. However, the liquid impervious sheet 12 may extend beyond both the side edges of the absorber 13 in the width direction or may extend between positions, which are away from both the side edges of the absorber 13 to the center side thereof in the width direction, respectively. As this liquid impervious sheet 12, it is desirable to use an opaque sheet so that brown color of excreta or urine is not seen. As opacification, a pigment or a filler such as calcium carbonate, titanium oxide, zinc oxide, white carbon, clay, talc, or barium sulfate added to plastic and formed into a film is preferably used.

It is preferable that three-dimensional gather parts 90 fit around the legs are formed on both side portions of the inner member 10. As illustrated in FIG. 5 and FIG. 6, each of the three-dimensional gather parts 90 includes a fixed portion 91 fixed to a side portion of the underside surface of the inner member 10, a main unit section 92 extending from the fixed portion 91 up to a side portion of a top surface of the inner member 10 through a side of the inner member 10, a fallen portion 93 formed by front and back end portions of the main unit section 92 fixed to the side portion of the top surface of the inner member 10 (top sheet 11 in the illustrated example) in a fallen state using a hotmelt adhesive 95*b*, etc., and a free portion 94 formed between parts of the fallen portion 93 to be unfixed. Each of these portions is formed of a gather sheet 95 that is a duplicate sheet obtained by folding a sheet such as a nonwoven fabric. The gather sheet 95 is attached over the entire inner member 10 in the front-back direction, the fallen portion 93 is provided on the front side and the back side of each of the non-absorber side portions 17, and the free portion 94 extends to both the front and back sides of each of the non-absorber side portions 17. In addition, between facing surfaces of the duplicate gather sheets 95, gather elastic members 96 are disposed at tip portions and the like of the free portion. As illustrated in FIG. 5, the gather elastic members 96 are for raising the free portion 94 by an elastic contraction force in a product state.

A fixing structure of the gather elastic members 96 and the gather sheet 95 is not particularly limited. For example, as in an example illustrated in FIG. 5 and FIG. 6, it is possible to adopt a structure described in the following. In portions other than the fallen portion 93, the gather elastic members 96 are attached and fixed to the gather sheet 95 through a hotmelt adhesive at positions of the gather elastic members 96, and facing surfaces of the gather sheet 95 are bonded to each other. However, in the fallen portion 93, the hotmelt adhesive is not present at the positions of the gather elastic members 96. Therefore, the gather elastic members 96 and the gather sheet 95 are not attached to each other, and the facing surfaces of the gather sheet 95 are not bonded to each other at positions having the gather elastic members 96.

As the gather elastic member 96, it is possible to use a normally used material such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less. Incidentally, as the gather elastic member 96, it is possible to use a tape-like member having a certain width in addition to an elongated member as in the illustrated example.

As a material of the gather sheet 95, various kinds of nonwoven fabrics may be used. However, in particular, in order to prevent stuffiness, it is preferable to use a nonwoven fabric that suppresses a basis weight and has excellent air permeability. Further, with regard to the gather sheet 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

As illustrated in FIG. 3 to FIG. 6, the underside surface of the inner member 10 is bonded to the internal surface of the outer member 20 by a hotmelt adhesive, etc. in an inner member fixing region 10B (shaded region). The range of the inner member fixing region 10B can be determined as appropriate and may cover almost the entire inner member 10. However, it is preferable that both ends of the inner member 10 in the width direction are not fixed to the outer member 20.

(Example of Outer Member)

The outer member 20 forms at least the lower torso region T of the front body part F and the lower torso region T of the back body part B. In the illustrated example, the outer member 20 further includes an intermediate region L corresponding to a range in the front-back direction between the lower torso region T of the front body part F and the lower torso region T of the back body part B. However, at least one of the front body part F and the back body part B may not include the intermediate region L. Referring to the outer member 20, as in the illustrated example, in the crotch portion, side edges of the outer member 20 may be located on a central side with respect to side edges of the inner member 10 in the width direction or located on an outer side thereof in the width direction.

A part located on the lower torso region T in the outer member 20 can be divided into a waist end portion 23 forming an end portion on a waist opening side and an under-waist portion U which is a portion lower than the waist end portion 23. When the outer member 20 has, in the part located on the lower torso region T, boundaries in each of which a stretching force in the width direction WD changes (boundaries in each of which e.g., the type, fineness, thickness, or stretch rate of the elastic member changes), a portion on the waist opening side of a boundary closest to the waist opening refers to the waist end portion 23. When there is no such a boundary, a portion extending from the absorber 13 or the inner member 19 on the waist opening side refers to the waist end portion 23. The lengths of these portions in the front-back direction LD can be determined as appropriate according to the size, type, etc. of the product.

In order to improve fitting to a body, in the outer member 20, a stretchable region 80, which is elastically stretching and contracting together with elastic members, may be formed by attaching the elastic members to appropriate sites. In a natural length state, the stretchable region 80 is contracted according to contraction of the elastic members such that wrinkles or pleats are formed. Then, the stretchable region 80 may be stretched together with the elastic members to a predetermined maximum elongation so as to be spread without forming wrinkles. As the elastic member, a known elongated elastic member such as a thread shaped elastic member and a belt shaped elastic member may be used. In addition to these members, it is also possible without any particular limitation to use an elastic sheet 30 such as elastic film and a nonwoven fabric made of elastomeric fibers. It is preferable that a plurality of stretchable regions 80 is provided at individual sites located in the waist end portion 23, the under-waist portion U and the intermediate region L. However, as can be known from a non-stretchable region 70 discussed below, the stretchable region 80 may be partially omitted at a middle portion thereof in the width direction WD, a middle portion thereof in the front-back direction LD, etc.

(Example of Stretchable Structure by Elastic Sheet)

In the outer member 20 of the illustrated example, except for a part located in a portion of the intermediate region L, as illustrated in FIG. 2 and FIG. 4 to FIG. 6, the elastic sheet 30 is interposed between a first sheet layer 20A and a second sheet layer 20B, and as illustrated in FIG. 9, the outer member 20 has an elastic sheet stretchable structure 20X in which the first sheet layer 20A and the second sheet layer 20B are bonded through joint holes 31 penetrating the elastic sheet 30 at a large number of joined portions 40 arranged at intervals. Further, a region having this elastic sheet stretchable structure 20X includes the stretchable region 80 that contracts in the width direction by contraction of the elastic sheet 30 and is extensible in the width direction (that is, the stretchable direction ED is the width direction WD of the diaper).

A planar shape of the outer member 20 is formed by concave around-leg lines 29 so that both side edges of the intermediate region L in the width direction form leg openings, respectively, and has a shape similar to an hourglass as a whole. The outer member 20 may be formed separately in the front body part F and the back body part B, and both bodies may be disposed to be separated in the front-back direction LD of the diaper at the crotch portion.

An embodiment illustrated in FIG. 1 and FIG. 2 is an embodiment in which the elastic sheet stretchable structure 20X extends to the waist end portion 23. However, the elastic sheet stretchable structure 20X used for the waist end portion 23 may cause insufficient tightening to the waist end portion 23. Therefore, as illustrated in FIG. 7 and FIG. 8, in the waist end portion 23, the elastic sheet stretchable structure 20X is not provided, and a stretchable structure by conventional elongated waist end portion elastic members 24 can be provided as necessary. The waist end portion elastic members 24 are elongated elastic members such as a plurality of rubber threads arranged at intervals in the front-back direction LD, and the waist end portion elastic members 24 apply a stretching force to tighten a waist circumference of the body. The waist end portion elastic members 24 are not disposed substantially in a bundle at close intervals, and three or more waist end portion elastic members 24, preferably five or more waist end portion elastic members 24 are disposed at intervals of about 3 to 8 mm in the front-back direction to form a predetermined stretchable zone. A stretch rate of the waist end portion elastic members 24 at the time of fixing can be determined as appropriate, and may be set to about 230 to 320% for a normal adult. As the waist end portion elastic members 24, rubber threads are used in the illustrated example. However, other elongated elastic members such as flat rubber may be used. Although not illustrated, the elastic sheet 30 may be provided at the waist end portion 23, and the elongated waist end portion elastic members 24 may be provided at positions overlapping the elastic sheet 30, so that a stretchable structure using both elastic members can be provided. In addition, in the illustrated embodiment, the elongated elastic members extending along leg openings are not provided in the edge portions of the leg openings in the outer member 20, but the elongated elastic members may be provided at positions overlapping the elastic sheet 30 in the edge portions or instead of the elastic sheet 30 of the edge portions.

As other embodiments, although not illustrated, appropriate modifications can be made. For example, the elastic sheet stretchable structure 20X may not be provided in the intermediate region L, the elastic sheet stretchable structure 20X may be continuously provided in the front-back direction LD from the inside of the lower torso region T of the front body part F to the inside of the lower torso region T of the back body part B via the intermediate region L, or the elastic sheet stretchable structure 20X may be provided only in one of the front body part F and the back body part B.

(Stretchable Region)

A region having the elastic sheet stretchable structure 20X in the outer member 20 has the stretchable region 80 that can be stretched and contracted in the width direction WD. The stretchable region 80 contracts in the width direction WD by a contraction force of the elastic sheet 30 and is extensible in the width direction WD. More specifically, in a state where the elastic sheet 30 is stretched in the width direction WD, the first sheet layer 20A and the second sheet layer 20B are bonded through the joint holes 31 of the elastic sheet 30 at intervals in each of the width direction WD and the front-back direction LD orthogonal thereto (the direction LD orthogonal to the stretchable direction ED) to form a large number of the joined portions 40, thereby forming the elastic sheet stretchable structure 20X. Further, in the stretchable region 80, the elastic sheet 30 is left without disconnection in the width direction WD, and the joined portions 40 are disposed such that the first sheet layer 20A and the second sheet layer 20B contract by the contraction force of the elastic sheet 30 and contraction pleats 25 are formed, thereby imparting such elasticity.

The stretchable region 80 may have portions 32 in each of which the elastic sheet 30 is linearly continuous along the width direction WD as in an example illustrated in FIG. 9 or may not have such portions 32 as in an example illustrated in FIG. 11 and an example illustrated in FIG. 15.

In the stretchable region 80, the first sheet layer 20A and the second sheet layer 20B between the joined portions 40 swell in a direction in which they are separated from each other, thereby forming the contraction pleats 25 extending in the front-back direction LD in the natural length state as illustrated in FIG. 9, and FIG. 14(*b*). Further, in the worn state of being stretched to some extent in the width direction WD, the contraction pleats 25 are left even though the contraction pleats 25 are extended. In addition, as in the illustrated embodiment, since the first sheet layer 20A and the second sheet layer 20B are not bonded to the elastic sheet 30 at least in a portion other than between the first sheet layer 20A and the second sheet layer 20B in the joined portions 40, as can be seen from FIG. 9(*c*) assuming a worn state and FIG. 9(*a*) assuming a spread state of the first sheet layer 20A and the second sheet layer 20B, in these states, edges of the joint holes 31 in the elastic sheet 30 are separated from outer peripheral edges of the joined portions 40 in the stretchable direction ED, respectively, so that vent holes 33 (gaps) are formed so as to open. Thus, even when the material of the elastic sheet 30 is a non-porous film or sheet, air permeability is imparted by the vent holes 33. In particular, in the case where the elastic sheet 30 has the portions 32 linearly continuous along the width direction WD, the joint holes 31 narrow due to further contraction of the elastic sheet 30 and a gap is hardly formed between the joint holes 31 and the joined portions 40 in the natural length state. On the other hand, in the case where the elastic sheet 30 does not have the portions linearly continuous along the width direction WD, the vent holes 33 are left.

It is desirable that a maximum elongation in the width direction WD of the stretchable region 80 is 190% or more (preferably 200 to 220%). Basically, the maximum elongation of the stretchable region 80 is substantially determined by the stretch rate of the elastic sheet 30 at the time of manufacture. However, the maximum elongation decreases due to factors that inhibit contraction in the width direction WD based thereon. A main factor of such inhibition is a ratio of the length L of the joined portions 40 per unit length in the width direction WD, and the maximum elongation decreases as this ratio increases. In a normal case, since the length L of the joined portions 40 has a correlation with an area ratio of the joined portions 40, the maximum elongation of the stretchable region 80 can be adjusted by the area ratio of the joined portions 40.

As in the examples illustrated in FIG. 9, in the case where the elastic sheet 30 has the portions 32 linearly continuous along the width direction WD, the stretching stress of the stretchable region 80 can be adjusted mainly by a sum of dimensions 32*w* orthogonal to the width direction WD (equal to intervals 31*d* of the joint holes 31) of the portions 32 in each of which the elastic sheet 30 is linearly continuous along the width direction WD (see FIG. 9(*a*)). On the other hand, as in the example illustrated in FIG. 11 and the example illustrated in FIG. 15, in the case where the elastic sheet 30 does not have the portions linearly continuous along the width direction WD, the stretching stress of the stretchable region 80 can be adjusted by an intersecting angle θ1 between the stretchable direction ED and the continuous direction of non-joint band 51, and an intersecting angle θ2 between the stretchable direction ED and the continuous direction of non-joint band 52. Here, in each of the non-joint bands 51, 52, a portion not having the joined portions 40 is continuous. In a normal case, it is preferable that the acute intersecting angle θ1 between the stretchable direction ED and the continuous direction of the non-joint band 51, and the acute intersecting angle θ2 between the stretchable direction ED and the continuous direction of the non-joint band 52, in the spread state, are set to be more than 0 degrees and 45 degrees or less, particularly a range of 10 to 30 degrees.

The area ratio of the joined portions 40 and the area of each of the joined portions 40 in the stretchable region 80 can be determined as appropriate and are preferably within the following ranges in a normal case.

Area of each of the joined portions 40: 0.14 to 3.5 $mm^2$ (particularly 0.14 to 1.0 $mm^2$)

Area ratio of the joined portions 40: 1.8 to 19.1% (particularly 1.8 to 10.6%)

As described above, the maximum elongation and stretching stress of the stretchable region 80 can be adjusted by the area of each of the joined portions 40. Thus, as illustrated in FIG. 7, a plurality of regions having different area ratios of the joined portions 40 may be provided in the stretchable region 80 to change fitting according to the site. In the embodiment illustrated in FIG. 7, edge portion regions 81 of leg openings correspond to a flexibly stretching and contracting region in which the area ratio of the joined portions 40 is high comparing to other regions in the stretchable region 80, and thus the stretching stress is weak.

A shape of each of the joined portions 40 and a shape of each of the joint holes 31 in the natural length state can be determined as appropriate, and may be set to any shape such as a perfect circle, an ellipse, a polygon such as a triangle, a rectangle (see FIG. 9, FIG. 11 and FIG. 15), or a rhombus (see FIG. 10(*b*)), a convex lens shape (see FIG. 10(*a*)), a concave lens shape (see FIG. 10(*c*)), a star shape, a cloud shape, etc. The dimensions of the individual joined portions 40 are not particularly limited. However, a maximum length 40*y* (approximately equal to a dimension 31*y* of each of the joint holes 31 in the orthogonal direction to the stretchable direction) is preferably 0.5 to 3.0 mm, particularly preferably 0.7 to 1.1 mm, and a maximum width 40*x* is preferably 0.1 to 3.0 mm, particularly 0.1 to 1.1 mm in the case of a shape that is long in a direction XD orthogonal to the stretchable direction ED.

An arrangement pattern of the joined portions 40 in the stretchable region 80 is not particularly limited and any pattern (see for example, Patent Literatures 1 to 8) can be adopted. In particular, as in the example illustrated in FIG. 9, as in the example illustrated in FIG. 11, and as in the example illustrated in FIG. 15, it is preferable that the non-joint bands 51 and 52 in each of which the portion not having the joined portions 40 is continuous are formed in an oblique lattice shape. The examples illustrated in the drawings are particularly preferable. That is, in each of these examples, in the stretchable region 80, as the non-joint bands 51 and 52 in each of which the portion not having the joined portions 40 is continuous, in the spread state, a first non-joint band 51 linearly continuous along a first direction 51*d* intersecting the stretchable direction ED at an acute angle (the acute intersecting angle θ1) is repeatedly present at intervals in a direction orthogonal to the first direction 51*d*. In addition, a large number of the joined portions 40 and joint holes 31 are provided at intervals between adjacent first non-joint bands 51 in the stretchable region 80. Further, characteristically, a unit structure including a plurality of first non-joint bands 51 having different first widths 51*w* determined as widths in the direction orthogonal to the first direction 51*d* is repeatedly present in the direction orthogonal to the first direction 51*d* in the stretchable region 80.

As described above, when the unit structure including the plurality of first non-joint bands 51 having different first widths 51*w* is repeatedly present in the direction orthogonal to the first direction 51*d* in the stretchable region 80, a similar magnitude change in width is formed in continuous portion of the elastic sheet 30 inside the first non-joint bands 51. That is, when the width 51*w* of the first non-joint bands 51 is narrow, the width of the continuous portion of the elastic sheet 30 on the inside is narrowed. In addition, when the width 51*w* of the first non-joint bands 51 is wide, the width of the continuous portion of the elastic sheet 30 on the inside is widened. Further, when there is a change in the first width 51*w* in the continuous portion of the elastic sheet 30 in the first non-joint bands 51, both the continuous portion of the elastic sheet 30 in the first non-joint band 51 having a wide width and the continuous portion of the elastic sheet 30 in the first non-joint bands 51 having a narrow width are visually emphasized. As a result, regardless of whether the stretchable region 80 is in the natural length state (see FIG. 13 and FIG. 17) or in the worn state stretched to some extent, an appearance having beautiful oblique stripe patterns is exhibited. That is, in a state of being contracted to some extent, a size of the contraction pleats 25 in the first non-joint bands 51 changes according to the first width 51*w* of the first non-joint band 51, and thus an oblique stripe pattern appears more clearly due to an influence of the contraction pleats 25.

The unit structure described above is not limited by the magnitude of the width 51*w* as long as the plurality of first non-joint bands 51 having different first widths 51*w* is included. However, it is preferable that a large first width 51*w* in the first non-joint bands 51 is 1.2 to 60 times that of a first non-joint band 51 having a closest width 51*w* and a small first width 51*w* is 0.01 to 0.8 times that of the first non-joint band 51 having the closest width 51*w*.

In addition, in the unit structure described above, as long as the plurality of first non-joint bands 51 having the different first widths 51*w* is included, the first widths 51*w* in all the first non-joint bands 51 may be different from each other, and a first width 51*w* in some of the plurality of first non-joint bands 51 may be different from a first width 51*w* of one or a plurality of other first non-joint bands 51 as illustrated in the figure.

Even if an oblique stripe pattern along the first direction 51*d* due to the contraction pleats 25 of the first non-joint bands 51 and the continuous portion of the elastic sheet 30 therein appears in the stretchable region 80, when an oblique stripe pattern along another oblique direction is more strongly visually recognized in the same stretchable region 80, there is concern that the oblique stripe pattern due to the contraction pleats 25 of the first non-joint bands 51 and the continuous portion of the elastic sheet 30 therein becomes inconspicuous. On the other hand, it is preferable that a maximum value of the first widths 51*w* in the first non-joint bands 51 is a maximum value of widths in a direction orthogonal to a continuous direction in all the non-joint bands 51 and 52 having same or different inclination directions since an oblique stripe pattern due to the contraction pleats 25 of the first non-joint bands 51 and the continuous portion of the elastic sheet 30 therein is more strongly visually recognized in the stretchable region 80. In this case, the maximum value of the first widths 51*w* in the first non-joint bands 51 can be determined as appropriate, and is preferably 1.2 to 60 times that of the first non-joint band 51 having the closest width 51*w*. Incidentally, widths of all the non-joint bands 51 and 52 including the first non-joint bands 51 in the direction orthogonal to the continuous direction are not limited and are preferably within a range of 0.02 to 5 mm in a normal case. Naturally, with regard to the widths of the non-joint bands 51 and 52, for example, the widths of the first non-joint bands 51 in the direction orthogonal to the continuous direction thereof correspond to the first widths 51*w*, and each of these width has a constant value, because these non-joint bands 51 and 52 are linearly continuous portions.

A first interval 51*s* determined as an interval between the adjacent first non-joint bands 51 in the direction orthogonal to the first direction 51*d* can be determined as appropriate. Therefore, the first interval 51*s* may be the same as, wider than, or narrower than the first width 51*w* of the adjacent first non-joint bands 51. As one preferable example, it is possible to mention a mode in which the maximum value of the first widths 51*w* of the first non-joint bands 51 is smaller than a maximum value of the first interval 51*s* in the unit structure. In this way, by forming a wide interval portion in the unit structure, the oblique stripe pattern due to the contraction pleats 25 of the first non-joint bands 51 and the continuous portion of the elastic sheet 30 therein is more strongly visually recognized. In this case, the maximum value of the first widths 51*w* of the first non-joint bands 51 can be determined as appropriate, and is preferably 0.01 to 9 times the maximum value of the first interval 51*s*. Incidentally, intervals between all the non-joint bands 51 and 52 including the first non-joint bands 51 in the direction orthogonal to the continuous direction are not particularly limited and are preferably within a range of 0.3 to 50 mm in a normal case. Naturally, with regard to the intervals between the adjacent non-joint bands 51 and between the adjacent non-joint bands 52, for example, the intervals between the adjacent first non-joint bands 51 in the direction orthogonal to the continuous direction thereof correspond to the first intervals 51*s*, and each of these intervals has a constant value along the continuous direction.

In the stretchable region 80, with regard to non-joint bands 51 and 52, the second non-joint bands 52 linearly continuous along a second direction 52*d* intersecting the stretchable direction ED at an acute angle (acute intersecting angle θ2) other than the first direction 51*d* may be repeatedly present at intervals in a direction orthogonal to the second direction 52*d*, or the second non-joint bands 52 may not be present. In one preferable mode having the second non-joint bands 52, the non-joint bands 51 and 52 are formed in an oblique lattice shape in the stretchable region 80, the first non-joint bands 51 are continuous portions in one direction in the non-joint bands 51 and 52 having the oblique lattice shape, and the second non-joint bands 52 are continuous portions in another direction in the non-joint bands 51 and 52 having the oblique lattice shape. In this case, the first direction 51*d* and the second direction 52*d* are opposite to each other in terms of inclination with respect to the stretchable direction ED. Incidentally, as in the example illustrated in FIG. 11 and the example illustrated in FIG. 15, even in a mode not having the non-joint bands 51 and 52 continuous in the width direction WD (stretchable direction ED), when each of the acute intersecting angles θ1 and θ2 between the stretchable direction ED and the first and second directions 51*d* and 52*d* is 5 to 45 degrees, particularly 10 to 30 degrees in the spread state of the stretchable region 80, elasticity in the stretchable region 80 can be sufficiently ensured.

However, when an oblique stripe pattern along an oblique direction of the second non-joint bands 52 is more strongly visually recognized in the same stretchable region 80, there is concern that the oblique stripe pattern due to the contraction pleats 25 of the first non-joint bands 51 and the continuous portion of the elastic sheet 30 therein becomes inconspicuous. Therefore, in the case where the second non-joint bands 52 are present as in the example illustrated in FIG. 15, it is desirable that all the second widths 52*w* determined as a width in the direction orthogonal to the second direction 52*d* in the second non-joint bands 52 are the same, or the joined portions 40 are disposed so that the second non-joint bands 52 are not present. In this way, in the stretchable region 80, the oblique stripe pattern due to the contraction pleats 25 of the first non-joint bands 51 and the continuous portion of the elastic sheet 30 inside thereof is more strongly visually recognized.

Meanwhile, between adjacent first non-joint bands 51, the joined portions 40 are aligned in the first direction 51*d*. In this case, for example, as illustrated in FIG. 16, it is preferable that all the joined portions 40 have an elongated shape in which an acute intersecting angle θ3 between the longitudinal direction and the direction orthogonal to the stretchable direction ED is within 10 degrees and a maximum dimension 40*e* in the stretchable direction ED is 0.1 to 0.4 mm since it is possible to ensure a larger dimension of the first non-joint bands 51 in the stretchable direction ED and to suppress a decrease in elasticity.

In addition, as in the example illustrated in FIG. 11, when the unit structure includes a plurality of first wide non-joint bands 51 having a maximum first width 51*w* and a plurality of first narrow non-joint bands 51 having a narrower first width 51*w* adjacent to each other in the direction orthogonal to the first direction 51*d*, it is preferable that each of the joined portions 40 having an elongated shape in which the acute intersecting angle between the longitudinal direction and the second direction 52*d* is within 5 degrees and a maximum dimension 40*f* in the direction orthogonal to the longitudinal direction is 0.1 to 0.4 mm are aligned at intervals in the first direction 51*d* between the adjacent first wide non-joint bands 51. In addition, it is preferable that each of the joined portions 40 having an elongated shape in which the acute intersecting angle θ3 between the longitudinal direction and the first direction 51*d* is 45 degrees or more and a maximum dimension 40*g* in the direction orthogonal to the longitudinal direction is 0.1 to 0.4 mm are aligned at intervals in the first direction 51*d* between the adjacent first narrow non-joint bands 51. By such a shape and arrangement of the joined portions 40, the contraction pleats 25 of the first non-joint bands 51 and the continuous portion of the elastic sheet 30 therein are particularly visually emphasized due to the smaller area of each of the joined portions 40.

One row or a plurality of rows of the joined portions 40 (rows in the continuous direction of the non-joint bands 51 and 52) may be located between the adjacent non-joint bands 51 and 52. In addition, it is preferable that intervals between the joined portions 40 in a row direction are regular. However, all the intervals may not be constant, and some intervals may be different.

(Non-Stretchable Region)

In a region having the elastic sheet stretchable structure 20X in the outer member 20, as illustrated in FIG. 7, the non-stretchable region 70 may be provided at least on one side of the stretchable region 80 in the width direction. The non-stretchable region 70 means that a maximum elongation in the stretchable direction ED is 120% or less. The maximum elongation of the non-stretchable region 70 is preferably 110% or less, and more preferably 100%. Arrangement of the stretchable region 80 and the non-stretchable region 70 can be determined as appropriate. In the case of the outer member 20 of the underpants-type disposable diaper as in the present example, a portion overlapping the absorber 13 is a region not requiring high elasticity. Thus, as in the illustrated embodiment, it is preferable to form a part or all of the portion overlapping the absorber 13 (it is desirable to include almost the entire inner member fixing region 10B) into the non-stretchable region 70. Naturally, the non-stretchable region 70 may be provided from a region overlapping the absorber 13 to a region not overlapping the absorber 13 away from the region in the width direction WD or the front-back direction LD, and the non-stretchable region 70 may be provided only in the region not overlapping the absorber 13.

The shape of each of the joined portions 40 in the non-stretchable region 70 is not particularly limited, and may be appropriately selected from the same shapes as those described in the section of the stretchable region 80.

In addition, the area ratio of the joined portions 40 and the area of each of the joined portions 40 in the non-stretchable region 70 can be determined as appropriate. However, in a normal case, the area ratio and the area are preferably within the following ranges since the non-stretchable region 70 does not become hard due to the small area of each of the joined portions 40 and the low area ratio of the joined portions 40.

Area of each of the joined portions 40: 0.10 to 0.75 $mm^2$ (particularly 0.10 to 0.35 $mm^2$)

Area ratio of the joined portions 40: 4 to 13% (particularly 5 to 10%)

The non-stretchable region 70 can be formed by densely disposing the joined portions 40 so that the first sheet layer 20A and the second sheet layer 20B are prevented from being contracted by the contraction force of the elastic sheet 30 to form pleats. Specific examples of a method for forming the non-stretchable region 70 include those shown in, for example, Patent Literatures 3 to 6. FIG. 25 and FIG. 26 illustrate an example of the non-stretchable region 70 disclosed in Patent Literature 6. Although the elastic sheet 30 has been originally continuous along the stretchable direction ED, in this non-stretchable region 70, the joint holes 31 are arranged densely at least to a certain degree in a staggered shape such that the elastic sheet 30 does not, due to the presence of these joint holes 31, have the portions linearly continuous along the stretchable direction ED. In this case, as shown in FIG. 25 and FIG. 26, in both the natural length state and the spread state, the vent holes (gaps) 33 are formed so as to open with a substantially the same size.

(Bonding Structure of Joined Portions)

When the first sheet layer 20A and the second sheet layer 20B are bonded in the joined portions 40 through the joint holes 31 formed in the elastic sheet 30, it is desirable that neither the first sheet layer 20A nor the second sheet layer 20B is bonded to the elastic sheet 30 except at least between the first sheet layer 20A and the second sheet layer 20B in the joined portions 40.

Means for bonding the first sheet layer 20A and the second sheet layer 20B in the joined portions 40 is not particularly limited. For example, in the joined portions 40, the first sheet layer 20A and the second sheet layer 20B may be bonded with a hot melt adhesive or may be bonded by means of material welding such as heat sealing or ultrasonic sealing.

In a case in which the first sheet layer 20A and the second sheet layer 20B are bonded through the joint holes 31 of the elastic sheet 30 in the joined portions 40, as a mode in which the joined portions 40 are formed by material welding, it is possible to adopt any one of a first welding mode, a second welding mode and a third welding mode, as follows. In the first welding mode, the first sheet layer 20A and the second sheet layer 20B are bonded only by a molten and solidified material 20*m* of a most part or a part of at least one of the first sheet layer 20A and the second sheet layer 20B in the joined portions 40 (see FIG. 18(*a*)). In the second welding mode, the first sheet layer 20A and the second sheet layer 20B are bonded only by a molten and solidified material 30*m* of all, a most part, or a part of the elastic sheet 30 in the joined portions 40 (see FIG. 18(*b*)). In the third welding mode, both of these modes are combined (see FIG. 18(*c*)). Among these modes, the second and third welding modes are preferable.

A particularly preferable mode is that the first sheet layer 20A and the second sheet layer 20B are bonded by the molten and solidified material 20*m* of the part of the first sheet layer 20A and the second sheet layer 20B and a molten and solidified material 30*m* of all or the most part of the elastic sheet 30 in the joined portions 40. Incidentally, in the third welding mode illustrated in FIG. 20(*b*), the molten and solidified material 30*m* of the elastic sheet 30 shown in white is seen among the molten and solidified material 20*m* of fibers in the first sheet layer 20A or the second sheet layer 20B shown in black. On the other hand, in the first welding mode illustrated in FIG. 20(*a*), the molten and solidified material 30*m* of the elastic sheet 30 is not seen among the molten and solidified material 20*m* of the fibers in the first sheet layer 20A or the second sheet layer 20B.

When the first sheet layer 20A and the second sheet layer 20B are bonded using the molten and solidified material 20*m* of the most part or the part of at least one of the first sheet layer 20A and the second sheet layer 20B as an adhesive as in the first welding mode or the third welding mode, it is preferable that a part of the first sheet layer 20A and the second sheet layer 20B is not melted since the joined portions 40 are not hardened.

Incidentally, when the first sheet layer 20A and the second sheet layer 20B are nonwoven fabrics, a case in which a part of the first sheet layer 20A and the second sheet layer 20B does not melt includes a mode in which cores (not only cores in composite fibers, but also central parts in single component fivers) of all fibers do not melt but surrounding parts thereof (not only sheath in composite fibers, but also surrounding parts in single component fivers) melt, or a mode in which some fibers do not melt at all while remaining fibers totally melt or while cores of the remaining fibers are left but surrounding parts thereof melt.

When the first sheet layer 20A and the second sheet layer 20B are bonded using the molten and solidified material 30*m* of the elastic sheet 30 as an adhesive like the second welding mode and the third welding mode, the peel strength becomes high. In the second welding mode, under a condition that a melting point of at least one of the first sheet layer 20A and the second sheet layer 20B is higher than a melting point of the elastic sheet 30 and a heating temperature at the time of forming the joined portions 40, the elastic sheet 30 is sandwiched between the first sheet layer 20A and the second sheet layer 20B, and portions to be the joined portions 40 are pressurized and heated such that only the elastic sheet 30 is melted at the time of manufacture.

On the other hand, in the third welding mode, under a condition that a melting point of at least one of the first sheet layer 20A and the second sheet layer 20B is higher than the melting point of the elastic sheet 30, the elastic sheet 30 is sandwiched between the first sheet layer 20A and the second sheet layer 20B, and portions to be the joined portions 40 are pressurized and heated such that at least one of the first sheet layer 20A and the second sheet layer 20B and the elastic sheet 30 are melted at the time of manufacture.

From such a viewpoint, the melting point of the elastic sheet 30 is preferably about 80 to 145° C., and the melting point of the first sheet layer 20A and the second sheet layer 20B is preferably about 85 to 190° C., particularly preferably 150 to 190° C. The difference between the melting points of the first sheet layer 20A and the second sheet layer 20B and the melting point of the elastic sheet 30 is preferably about 60 to 90° C. The heating temperature is preferably about 100 to 150° C.

In the second welding mode and the third welding mode, when the first sheet layer 20A and the second sheet layer 20B are nonwoven fabrics, the molten and solidified material 30*m* of the elastic sheet 30 may penetrate between fibers over the entire first sheet layer 20A and second sheet layer 20B in a thickness direction in the joined portions 40 as illustrated in FIG. 19(*c*). However, in a mode in which the molten and solidified material 30*m* penetrates between the fibers to the middle in the thickness direction as illustrated in FIG. 19(*a*), or a mode in which the molten and solidified material 30*m* hardly penetrates between the fibers of the first sheet layer 20A and the second sheet layer 20B as illustrated in FIG. 19(*b*), flexibility of the joined portions 40 becomes high.

FIG. 21 illustrates an example of an ultrasonic sealing device suitable for forming the second welding mode and the third welding mode. In this ultrasonic sealing device, when the joined portions 40 are formed, the first sheet layer 20A, the elastic sheet 30, and the second sheet layer 20B are fed between an anvil roll 60 having projections 60*a* formed in the pattern of the joined portions 40 on an outer surface and an ultrasonic horn 61. At this time, for example, by setting a feeding speed of the elastic sheet 30 on an upstream side by a feed drive roll 63 and a nip roll 62 to be lower than a feeding speed on a downstream side of the anvil roll 60 and the ultrasonic horn 61, the elastic sheet 30 is stretched to a predetermined stretch rate in an MD (machine direction, flow direction) through a path from a nip position by the feed drive roll 63 and the nip roll 62 to a seal position by the anvil roll 60 and the ultrasonic horn 61. The stretch rate of the elastic sheet 30 can be set by selecting a speed difference between the anvil roll 60 and the feed drive roll 63, and can be set to about 300% to 500%, for example.

The first sheet layer 20A, the elastic sheet 30, and the second sheet layer 20B fed between the anvil roll 60 and the ultrasonic horn 61 are heated by ultrasonic vibration energy of the ultrasonic horn 61 while being pressurized between the projections 60*a* and the ultrasonic horn 61 in a state of being stacked in this order. By melting only the elastic sheet 30 or melting at least one of the first sheet layer 20A and the second sheet layer 20B and the elastic sheet 30, the joint holes 31 are formed in the elastic sheet 30. At the same time, the first sheet layer 20A and the second sheet layer 20B are bonded through the joint holes 31. Therefore, in this case, by selecting a size, a shape, a separation interval, and an arrangement pattern in a roll length direction and a roll circumferential direction of the projections 60*a* of the anvil roll 60, it is possible to select an area ratio of the joined portions 40.

A reason why the joint holes 31 are formed may not be clear. However, it is considered that the holes are formed when portions corresponding to the projections 60*a* of the anvil roll 60 in the elastic sheet 30 are melted and detached from the surroundings. In this instance, as illustrated in FIG. 9(*a*), FIG. 12 and FIG. 13, in the elastic sheet 30, a portion, which is disposed between adjacent joint holes 31 aligned in the stretchable direction ED, is cut from portions on both sides in the stretchable direction ED by the joint holes 31, and loses support on both sides in a contracting direction. Thus, in a range in which continuity in a direction orthogonal to the contracting direction is secured, the portion, which is disposed between adjacent joint holes 31 aligned in the stretchable direction ED, contracts more, with increasing proximity to a center side in the direction LD orthogonal to the stretchable direction ED, until this center side in the direction LD balances with a center side in the stretchable direction ED, and the joint holes 31 expand in the stretchable direction ED.

Although a constituent material of the first sheet layer 20A and the second sheet layer 20B is not particularly limited, it is preferable for the material to have air permeability. From the viewpoints, a nonwoven fabric may be preferably used. When the nonwoven fabric is used, the basis weight thereof is preferably about 10 to 25 g/m$^2$. Further, a part or the whole of the first sheet layer 20A and the second sheet layer 20B may be a pair of layers in which a single material is folded back to face each other. For example, as in the illustrated embodiment, in the waist end portion 23, the constituent material located on the outer side is regarded as the second sheet layer 20B, and the folded portion 20C folded back to the internal surface side at a waist opening edge is regarded as the first sheet layer 20A, and an elastic sheet 30 is interposed therebetween. In the other portions, the constituent material located on the inner side is regarded as the first sheet layer 20A, the constituent material located on the outer side is regarded as the second sheet layer 20B, and the elastic sheet 30 can be interposed therebetween. It is obvious that the constituent material of the first sheet layer 20A and the constituent material of the second sheet layer 20B can be individually provided over the entire front-back direction LD, and without folding back the constituent materials, the elastic sheet 30 may be interposed between the constituent material of the first sheet layer 20A and the constituent material of the second sheet layer 20B.

The elastic sheet 30 is not particularly limited. As long as it is made of a thermoplastic resin which has elasticity, it may be an elastic nonwoven fabric in addition to elastic film. Further, as the elastic sheet 30, in addition to an imperforate sheet, those having many holes and slits for ventilation can also be used. In particular, in the elastic sheet 30, the tensile strength in the width direction WD (stretchable direction ED, MD direction) is preferably 8 to 25 N/35 mm, the tensile strength in the front-back direction LD (direction XD orthogonal to the stretchable direction ED, CD direction) is preferably 5 to 20 N/35 mm, the tensile elongation in the width direction WD is preferably 450 to 1050%, and the tensile elongation in the front-back direction LD is preferably 450 to 1400%. The thickness of the elastic sheet 30 is not particularly limited, but it is preferably about 20 to 40 km.

(Stretchable Structure by Elongated Elastic Members)

Unlike the present example, in the outer member 20, a part or whole of the stretchable region 80, the non-stretchable region 70 as well as an intergluteal cleft stretchable region 82 and a sacrum stretchable region 83 discussed below may be provided by using elongated elastic members as in Patent Literature 2.

(Intergluteal Cleft Stretchable Region)

It is preferable that the intergluteal cleft stretchable region 82, which includes an intergluteal cleft elastic member (the elastic sheet 30 in the illustrated example) therein, is provided in the back body part B. The intergluteal cleft stretchable region 82 refers to a region extending over both sides of the second portion B2 in the width direction WD and both the side edges of the region are away from both imaginary straight lines to a center side thereof in the width direction WD, respectively, provided that the imaginary straight lines pass through both the first portions B1 along the front-back direction LD, respectively.

A position of the intergluteal cleft stretchable region 82 is changed according to dimensions and designs of the product. In a normal case, for example, it can be determined as follows. That is, in the spread state of the product from which the side seal portions 21 are removed by cutting along the edges thereof on the center side, respectively, assuming that the position of the edge of the waist opening of the front body part F corresponds to 0% and the position of the edge of the waist opening of the back body part B corresponds to 100%, the intergluteal cleft stretchable region 82 may be provided from a position in a range of 50 to 70% to a position in a range of 60 to 80%. In addition, in the spread state of the product (in the state in which the product is stretched to the maximum elongation in the width direction WD by pulling the product from both the side ends thereof while one of the side seal portions 21 and the other of the side seal portions 21 are pinched, respectively), assuming that the side edge of one of the side seal portions 21 of the back body part B corresponds to 0% and the side edge of the other of the side seal portions 21 of the back body part B corresponds to 100%, the intergluteal cleft stretchable region 82 may be provided from a position in a range of 40 to 60% to a position in a range of 50 to 70%.

In the illustrated example, a region, which is adjacent to the intergluteal cleft stretchable region 82 at both sides thereof in the width direction WD, refers to the non-stretchable region 70. However, as long as a maximum elongation in the width direction WD of the intergluteal cleft stretchable region 82 is larger than a maximum elongation in the width direction WD of a region, which is adjacent to the intergluteal cleft stretchable region 82 at both the sides thereof in the width direction WD, this region, which is adjacent to the intergluteal cleft stretchable region 82 at both the sides thereof in the width direction WD, may refer to the stretchable region 80. In addition, in the illustrated example, a region, which is provided on the waist opening side and a crotch portion side of the intergluteal cleft stretchable region 82, refers to the non-stretchable region 70. However, either one of or both of a part of the intergluteal cleft stretchable region 82 on the waist opening side and a part of the intergluteal cleft stretchable region 82 on the crotch portion side may refer to the stretchable region 80.

The maximum elongation in the width direction WD of the intergluteal cleft stretchable region 82 can be determined as appropriate. However, in a normal case, it may be preferably about 120 to 200%.

In particular, as in the illustrated example, in a case where, the intergluteal cleft stretchable region 82, the non-stretchable region 70, which is adjacent to the intergluteal cleft stretchable region 82 at both sides thereof in the width direction WD and located at the center side of both the side edges of the absorber 13 in the width direction WD, and a side stretchable region 80, which is adjacent to the non-stretchable region 70 at both sides thereof in the width direction WD and extended to outer sides of both the side edges of the absorber 13 in the width direction WD, are provided by a single elastic sheet stretchable structure 20X, it is preferable that a maximum elongation in the width direction WD of the non-stretchable region 70 is less than 120%, a maximum of the intergluteal cleft stretchable region 82 is 1.5 to 3 times the maximum elongation in the width direction WD of the non-stretchable region 70, and a maximum elongation of the side stretchable region 80 is 2 to 5 times the maximum elongation in the width direction WD of the non-stretchable region 70.

A shape of the intergluteal cleft stretchable region 82 can be determined as appropriate: such as a rectangular shape, which has a pair of sides along the front-back direction LD and a pair of sides along the width direction WD as shown in FIG. 24(*a*); a shape having a width becoming wider toward the back side (for example, such as an isosceles triangle with a base along the width direction WD and an apex at the front side of the base, like the sacrum stretchable region 83 illustrated in FIG. 22); and a quadrilateral shape, which is composed of a front side portion having a width becoming wider toward the back side and a back side portion tapered toward the back side and which has a diagonal along the front-back direction LD and a diagonal along the width direction WD intersecting each other as illustrated in FIG. 23(*a*), FIG. 23(*b*), and FIG. 24(*b*). In addition, the shape of the intergluteal cleft stretchable region 82 may be framed by straight lines or with a periphery a part or all of which is curved.

An elongation at an elastic limit of the intergluteal cleft stretchable region 82 may be changed or constant over entire the region 82. In particular, as the illustrated example, when the intergluteal cleft stretchable region 82 is formed by the elastic sheet stretchable structure 20X, as illustrated in FIG. 23(*a*), it is preferable that in a middle part of the intergluteal cleft stretchable region 82 in the front-back direction LD (or "in the whole of intergluteal cleft stretchable region 82" is possible), an area ratio of the joined portions 40 decreases stepwise (or "decreases continuously" is possible) from both side edges of the middle part toward the center thereof in the width direction WD, respectively. In this way, in the intergluteal cleft stretchable region 82, a percentage of contraction becomes higher toward the center thereof in the width direction WD. The intergluteal cleft stretchable region therefore becomes excellent particularly in the fitting to the intergluteal cleft. Incidentally, in the example illustrated in FIG. 23(*a*), the area ratio of the joined portions 40 in a center region 82A in the width direction WD is smaller than (for example, 0.1 to 0.9 times) the area ratio of the joined portions 40 in side regions 82B located at both sides of the center region 82A.

(Sacrum Stretchable Region)

It is preferable that in a third portion B3 in the back body part B, a sacrum stretchable region 83 having a sacrum elastic member therein is provided. In the illustrated example, a region, which is adjacent to the sacrum stretchable region 83 at both sides thereof in the width direction WD, refers to the non-stretchable region 70 discussed below. However, as long as a maximum elongation in the width direction WD of the sacrum stretchable region 83 is larger than a maximum elongation in the width direction WD of a region, which is adjacent to the sacrum stretchable region 83 at both the sides thereof in the width direction WD, this region, which is adjacent to the sacrum stretchable region 83 at both the sides thereof in the width direction WD, may refer to the stretchable region 80. In addition, in the illustrated example, a stretchable region 80, which is continuous in the width direction between both the side seal portions, is adjacent to the sacrum stretchable region 83 on the waist opening side thereof (that is, the stretchable region 80 is continuous from the sacrum stretchable region 83 on the waist opening side thereof), while a non-stretchable region 70 is adjacent thereto on a crotch portion side thereof. On the contrary, it is possible that the stretchable region 80 is adjacent thereto on the crotch portion side thereof, while the non-stretchable region 70 is adjacent thereto on the waist opening side thereof. Further, it is also possible that the stretchable region 80 or the non-stretchable region 70 is adjacent thereto on both the crotch portion side thereof and the waist opening side thereof.

A position of the sacrum stretchable region 83 is changed according to dimensions and designs of the product. In a normal case, for example, it may be determined as follows. That is, in the spread state of the product from which the side seal portions 21 are removed by cutting along the edges thereof on the center side, assuming that the position of the edge of the waist opening of the front body part F corresponds to 0% and the position of the edge of the waist opening of the back body part B corresponds to 100%, the sacrum stretchable region 83 may be provided from a position in a range of 60 to 80% to a position in a range of 70 to 90%. In addition, in the spread state of the product (in the state in which the product is stretched to the maximum elongation by pulling the product from both the side ends thereof while one of the side seal portions 21 and the other of the side seal portions 21 are pinched, respectively), assuming that the side edge of one of the side seal portions 21 of the back body part B corresponds to 0% and the side edge of the other of the side seal portions 21 of the back body part B corresponds to 100%, the sacrum stretchable region 83 may be provided from a position in a range of 40 to 60% to a position in a range of 50 to 70%.

The maximum elongation of the sacrum stretchable region 83 in the width direction WD can be appropriately determined, and may be the same as, larger than, or smaller than the maximum elongation of the intergluteal cleft stretchable region 82.

A shape of the sacrum stretchable region 83 refers preferably to a shape having a width becoming wider toward the back side (for example, such as an isosceles triangle with a base along the width direction WD and an apex at the front side of the base, like the example illustrated in FIG. 22), and can be a rectangular shape with a pair of sides along the front-back direction LD and a pair of sides along the width direction WD as the intergluteal cleft stretchable region 82 shown in FIG. 24(*a*). In addition, the shape of the sacrum stretchable region 83 may be surrounded by straight lines or a periphery a part or all of which is curved (for example, both the side edges of the sacrum stretchable region 83 in each of illustrated examples are depressed to the center side so as to be circular arc shaped).

(Slots of Absorber)

It is preferable that in the absorber 13, at both the sides of the intergluteal cleft stretchable region 82 in the width direction WD, slots 100 (elongated holes in a plan view penetrating the absorber 13 in the thickness direction) are formed to extend outwardly in the width direction WD toward the back side, respectively. In this way, even when a lifting force (indicated by open arrows outlined with alternate long and two short dashes lines) exerts alternately on both the sides of the intergluteal cleft stretchable region 82 in the width direction WD, the absorber 13 deforms such that the widths of the slots 100 are decreased (in a manner where the slots are closed), thus, the force can be absorbed. As a result, the unevenness, crack and twist of the absorber 13 at both the sides of the intergluteal cleft stretchable region 82 in the width direction WD can be suppressed, while the improved fitting to the intergluteal cleft can be attained by the intergluteal cleft stretchable region 82.

Shapes of the slots 100 can be determined as appropriate according to a shape of round-leg portions of the underpants-type disposable diaper and arrangements of various kinds of elastic members. For example, as shown in FIG. 23(*a*), the slot 100 on one side of the intergluteal cleft stretchable region 82 and the slot 100 on the other side thereof in the width direction WD may be connected to each other so as to form one hole, and as shown in FIG. 22, FIG. 23(*b*), FIG. 24(*a*) and FIG. 24(*b*), the slots 100 may not be connected to each other, so as to form separate holes. In addition, as shown in FIG. 22, FIG. 23(*a*), FIG. 23(*b*) and FIG. 24(*b*), the slots 100 may extend linearly (may be, for example, substantially rectangular shaped) and as shown in FIG. 24(*a*), the slots 100 may extend in curved lines (including bending lines) so as to have larger inclinations to the front-back direction LD toward the back side, respectively. Further, as shown in FIG. 22, FIG. 23(*a*), FIG. 23(*b*) and FIG. 24(*a*), widths 100*w* of the slots 100 (dimensions in the directions orthogonal to directions along which the slots extend) may be constant. Alternatively, as shown in FIG. 24(*b*), the slots 100 may have shapes which are tapered toward the front side so as to be, for example, triangle-shaped.

As long as the slots 100 are provided on both the sides of the intergluteal cleft stretchable region 82 in the absorber 13 in the width direction WD, as shown in FIG. 22, FIG. 23(*a*), FIG. 24(*a*) and FIG. 24(*b*), one slot may be provided in each side, or as shown in FIG. 23(*b*), a plurality of slots may be arranged at intervals in each side.

The widths 100*w* of the slots 100 may be determined as appropriate. As an example, the widths 100*w* of the slots 100 are preferably 0.05 to 0.2 times the maximum width 13*w* of the absorber 13, respectively.

The directions 101 along which the slots 100 extend can be determined as appropriate according to the shape of the round-leg portions of the underpants-type disposable diaper, shapes of the slots 100, and the arrangements of various kinds of the elastic members. However, in a normal case, acute intersecting angles $y_1$ between the front-back direction LD and the directions along which the slots 100 extend are preferably 10 to 75 degrees, particularly 30 to 60 degrees, respectively. As an example, the directions 101 along which the slots 100 extend are preferably parallel with the line segments connecting the first portions B1 and the front end of the second portion B2, respectively. Incidentally, the directions 101 along which the slots 100 extend refer to directions along which center lines of the slots 100 extend, respectively. Further, in a case where the directions along which the slots 100 extend are curved lines such as circular arcs, the directions along which the slots 100 extend refer to directions along which tangential lines of the center lines of the slots 100 extend, respectively.

Particularly, it is preferable that, as the illustrated example, those portions of both the side edges of the intergluteal cleft stretchable region 82, which correspond to both the slots 100 locating at least in the width direction WD, respectively, extend in parallel with directions along which both the slots 100 extend, respectively, because when the lifting force, which is generated by the backward movements of the legs, exerts, the absorber 13 may be deformed easily so as to, in particular, decrease the widths of the slots 100.

A positional relation between the side edges of the intergluteal cleft stretchable region 82 and the slots 100 can be determined as appropriate and the side edges of the intergluteal cleft stretchable region and the slots may be separated from each other, respectively. However, it is preferable that the above side edges and the slots are closer to each other (that is, intervals between the side edges of the intergluteal cleft stretchable region 82 and the slots 100 are smaller than intervals between the side edges of the absorber 13 and the slots 100), respectively, because when the lifting force, which is generated by the backward movements of the legs, exerts, the force may be applied easily, in particular, to the slots 100 of the absorber 13. As an example, intervals between edges of the slots 100 on the center side in the width direction WD and the side edges of the intergluteal cleft stretchable region 82 are preferably about 0 to 10 mm (If the intervals are not constant, minimum intervals are adopted). In addition, as long as the slots 100 are provided on both the sides of the intergluteal cleft stretchable region 82 in the width direction WD, the slots 100 may extend over a whole range or beyond the whole range corresponding to the intergluteal cleft stretchable region 82 in the front-back direction LD. Alternatively, as in the illustrated examples, the slots 100 may be provided at both sides of a part of the intergluteal cleft stretchable region 82 in the front-back direction LD. In the illustrated examples, the slots 100 are provided at both the sides of only the front side portion of the intergluteal cleft stretchable region 82 in the front-back direction LD. However, the slots 100 may be provided at both sides of only the back side portion of the intergluteal cleft stretchable region 82 in the front-back direction LD, or the slots 100 may be provided at both sides of only the middle part of the intergluteal cleft stretchable region 82 in the front-back direction LD.

Particularly, when the elastic sheet stretchable structure 20X as in the illustrated examples is adopted, if the non-stretchable region 70 having the maximum elongation of less than 120% in the width direction WD is adjacent to the intergluteal cleft stretchable region 82 at both the sides thereof in the width direction WD and the slots 100 are arranged only in the non-stretchable region 70 (a whole of each slot 100 is located within the non-stretchable region 70), the widths of the slots 100 become unlikely to be decreased in a situation where the lifting force, which is generated by the backward movements of the legs, does not exert. In this case, the widths of the slots 100 do not need to be increased to an excessive degree in order to prepare for a situation where the above lifting force exerts, and thereby decrease of an absorption amount may be prevented.

In a case where the sacrum stretchable region 83 is provided as discussed above, it is preferable that in the absorber 13, at both the sides of the sacrum stretchable region 83 in the width direction WD, the slots 100 (elongated holes in a plan view penetrating the absorber 13 in the thickness direction) are formed to extend outwardly in the width direction WD toward the back side, respectively. In this way, even when the lifting force exerts alternately on both the sides of the sacrum stretchable region 83 in the width direction WD, the absorber 13 deforms such that the widths of the slots 100 are decreased (in a manner where the slots 100 are closed), thus, the force can be absorbed. As a result, the unevenness, crack and twist of the absorber 13 at both the sides of the sacrum stretchable region 83 in the width direction WD can be suppressed, while the improved fitting to a dent formed on a body surface at the sacrum of the wearer can be attained by the sacrum stretchable region 83.

In a case where the slots 100 are provided at both the sides of the intergluteal cleft stretchable region 82 in the width direction WD and at both the sides of the sacrum stretchable region 83 in the width direction WD, it is preferable that acute inclination angles $\gamma_2$ between the front-back direction LD and the directions 101 along which the slots 100 provided at both the sides of the sacrum stretchable region 83 in the width direction WD extend are 0.3 to 0.8 times the acute intersecting angles $\gamma_1$ between the front-back direction LD and the directions 101 along which the slots 100 provided at both the sides of the intergluteal cleft stretchable region 82 in the width direction WD extend, respectively, because the slots 100 at respective positions become able to perform their own functions sufficiently.

DESCRIPTION OF TERMS IN SPECIFICATION

The following terms in the specification have the following meanings unless otherwise specified in the specification.

The "Front body part" and "back body part" refer to front side portion and back side portion, respectively, with respect to a center of the underpants-type disposable diaper in the front-back direction as a boundary. In addition, the crotch portion refers to a range in the front-back direction including the center of the underpants-type disposable diaper in the front-back direction, and refers to a range of a portion having the narrowing portion in the front-back direction when the absorber has the narrowing portion.

The "maximum elongation" refers to a maximum value of an elongation in the stretchable direction in an elastic deformation region (in other words, an elongation at an elastic limit, being equal to an elongation in the spread state) and represents a length in the spread state as a percentage when the natural length is 100%.

The "area ratio" refers to a ratio of a target portion to a unit area, and is represented as a percentage by dividing a total area of target portions (for example, the joined portions 40, the openings of the joint holes 31, and the vent holes) in target regions (for example, the stretchable region 80 and the non-stretchable region 70) by an area of the target regions. In particular, the "area ratio" in a region having the stretchable structure refers to an area ratio in the spread state. In a mode in which a large number of target portions are provided at intervals, it is desirable to obtain the area ratio by setting a size of the target regions to include ten or more target portions.

The "stretch rate" refers to a value when the natural length is 100%. For example, a stretch rate of 200% is synonymous with an elongation ratio of 2.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" of the absorber is measured using a thickness measuring instrument of Ozaki Mfg. Co., Ltd. (Peacock, Dial Thickness Gauge Large Type, Model J-B (measurement range 0 to 35 mm) or Model K-4 (measurement range 0 to 50 mm)) by horizontally placing the sample and the thickness measuring device.

A "thickness" other than the above thickness is automatically measured under the condition of load: 0.098 $N/cm^2$ and pressure area: 2 $cm^2$ using an automatic thickness meter (KES-G5 handy compression measurement program).

The "tensile strength" and the "tensile elongation (breaking elongation)" refer to values measured by setting an initial chuck interval (distance between marked lines) to 50 mm and a tensile speed to 300 mm/min in accordance with JIS K7127:1999 "Plastics-Determination of tensile properties-" except that the test piece has a rectangular shape of width 35 mm×length 80 mm. As a tensile testing machine, for example, AUTOGRAPH AGS-G100N manufactured by SHIMADZU CORPORATION can be used.

The "stretching stress" refers to the tensile stress (N/35 mm) measured when stretching in the elastic region by a tensile test setting an initial chuck interval (distance between marked lines) to 50 mm and a tensile speed to 300 mm/min in accordance with JIS K7127:1999 "Plastics-Determination of tensile properties-", and a degree of stretching may be determined as appropriate depending on the test object. It is preferable that the test piece has a rectangular shape having a width of 35 mm and a length of 80 mm or more. However, when a test piece having a width of 35 mm may not be cut out, the test piece is created to have a width allowing cutting out, and a measured value is set to a value converted to have the width of 35 mm. In addition, even in a case in which the target region is small and sufficient test pieces may not be collected, when the magnitude of stretching stress is compared, even a suitably small test piece can be compared at least as long as test pieces of the same size are used. As a tensile testing machine, for example, AUTOGRAPH AGS-G100N manufactured by SHIMADZU CORPORATION can be used.

The "spread state" refers to a flatly spread state without contraction (including any kinds of contraction such as contraction by an elastic member) or slack.

Dimensions of each portion refer to dimensions in a spread state rather than the natural length state unless otherwise stated.

When there is no description about an environmental condition in a test or measurement, it is presumed that the test or measurement is performed in a test room or a device in a standard state (temperature 23±1° C., relative humidity 50±2% in a test location).

INDUSTRIAL APPLICABILITY

The present invention can be used for general underpants-type disposable wearing articles such as a shorts-type sanitary napkin, an underpants-type disposable swimming wear for swimming or playing in the water, etc. in addition to the underpants-type disposable diaper as in the above example.

REFERENCE SIGNS LIST

10 Inner member
100 Slot
10B Inner member fixing region
11 Top sheet
12 Liquid impervious sheet
13 Absorber
13N Narrower portion
14 Wrapping sheet
17 Non-absorber side portion
20 Outer member
20A First sheet layer
20B Second sheet layer
20C Folded portion
20X Elastic sheet stretchable structure
21 Side seal portion
23 Waist end portion
24 Waist end portion elastic member
25 Contraction pleat
29 Around-leg line
30 Elastic sheet
31 Joint hole
33 Vent hole
40 Joined portion
51, 52 Non-joint band
51 First non-joint band
51*d* First direction
51*s* First interval
51*w* First width
52 Second non-joint band
52*d* Second direction
60 Anvil roll
61 Ultrasonic horn
70 Non-stretchable region
80 Stretchable region
82 Intergluteal cleft stretchable region
83 Sacrum stretchable region
90 Three-dimensional gather part
93 Fallen portion
94 Free portion
95 Gather sheet
96 Gather elastic member
B Back body part
B1 First portion
B2 Second portion
B3 Third portion
ED stretchable direction
F Front body part
L Intermediate region
LD Front-back direction
T Lower torso region
WD Width direction

The invention claimed is:

1. An underpants-type disposable wearing article comprising:

an outer member forming at least a lower torso region of a front body part and a lower torso region of a back body part;

an absorber provided from the front body part to the back body part; and side seal portions in which both side portions of the front body part and both side portions of the back body part are bonded to each other, respectively, to form a waist opening and a left-and-right-pair of leg opening portions, wherein the back body part includes a pair of first portions comprising first portion line segments extending along a front-back direction, wherein the pair of first portions are configured to face left and right gluteal peaks, respectively, and a second portion comprising a range of a center line passing through a center of the back body part in a width direction, which is configured to face an intergluteal cleft, an intergluteal cleft stretchable region bounded by four side edges and comprising an intergluteal cleft elastic member, wherein each of the four side edges are positioned outwardly of the second portion and inwardly of the first portion line segments in the width direction, the intergluteal cleft stretchable region stretches and contracts in the width direction between a natural length state where the intergluteal cleft elastic member is contracted, and a spread state where the intergluteal cleft elastic member is stretched, a maximum elongation in the width direction of the intergluteal cleft stretchable region is larger than a maximum elongation in the width direction of a region adjacent to the intergluteal cleft stretchable region on both sides thereof in the width direction, in the absorber, on both right and left sides of the intergluteal cleft stretchable region in the width direction, slots are formed to extend outwardly in the width direction toward a back side, respectively, and at least two of the four side edges of the intergluteal cleft stretchable region extend in directions that are parallel with directions along which the slots extend.

2. The underpants-type disposable wearing article according to claim 1, wherein acute intersecting angles between the front-back direction and the directions along which the slots extend are 30 to 70 degrees, respectively.

3. The underpants-type disposable wearing article according to claim 2, wherein the slots are adjacent to the intergluteal cleft stretchable region.

4. The underpants-type disposable wearing article according to claim 2, wherein the intergluteal cleft stretchable region includes a first sheet layer, a second sheet layer and an elastic sheet disposed therebetween as the intergluteal cleft elastic member, and the first sheet layer and the second sheet layer are bonded directly or indirectly at a large number of joined portions arranged at intervals, at least in a middle part of the intergluteal cleft stretchable region in the front-back direction, an area ratio of the joined portions decreases stepwise or continuously from both a right and a left side edges of the middle part toward the center thereof in the width direction, respectively.

5. The underpants-type disposable wearing article according to claim 2, wherein the back body part further comprises a non-stretchable region adjacent to the intergluteal cleft stretchable region and outwardly on both sides of the four side edges in the width direction, and a side stretchable region, which is adjacent to the non-stretchable region at both right and left sides thereof in the width direction and extended to outer sides of both right and left side edges of the absorber in the width direction, a region, which is provided from a part of the side stretchable region on one side, through a part of the non-stretchable region on one side, the intergluteal cleft stretchable region, and a part of the non-stretchable region on the other side, to a part of the side stretchable region on the other side includes a first sheet layer, a second sheet layer and an elastic sheet forming the intergluteal cleft elastic member and being disposed therebetween, and the first sheet layer and the second sheet layer are bonded directly or indirectly at a large number of joined portions arranged at intervals, a maximum elongation in the width direction of the non-stretchable region is less than 120%, a maximum elongation of the intergluteal cleft stretchable region is 1.5 to 3 times the maximum elongation in the width direction of the non-stretchable region, a maximum elongation of the side stretchable region is 2 to 5 times the maximum elongation in the width direction of the non-stretchable region, the slots are provided only in the non-stretchable region.

6. The underpants-type disposable wearing article according to claim 2, wherein the back body part includes a third portion comprising a part of the center line passing through the center of the back body part in the width direction and located in a range configured to face a sacrum, a sacrum stretchable region bounded by two sacrum side edges and comprising a sacrum elastic member is provided over both right and left sides of the third portion in the width direction, the sacrum stretchable region stretches and contracts in the width direction between a natural length state where the sacrum elastic member is contracted, and a spread state where the sacrum elastic member is stretched, a maximum elongation in the width direction of the sacrum stretchable region is larger than a maximum elongation in the width direction of a region, which is adjacent to the sacrum stretchable region on both sides thereof in the width direction, and in the absorber, on both right and left sides of the sacrum stretchable region in the width direction, slots are formed to extend outwardly in the width direction toward the back side, respectively.

7. The underpants-type disposable wearing article according to claim 1, wherein the slots are adjacent to the intergluteal cleft stretchable region.

8. The underpants-type disposable wearing article according to claim 7, wherein the intergluteal cleft stretchable region includes a first sheet layer, a second sheet layer and an elastic sheet disposed therebetween as the intergluteal cleft elastic member, and the first sheet layer and the second sheet layer are bonded directly or indirectly at a large number of joined portions arranged at intervals, at least in a middle part of the intergluteal cleft stretchable region in the front-back direction, an area ratio of the joined portions decreases stepwise or continuously from both a right and a left side edge of the middle part toward the center thereof in the width direction, respectively.

9. The underpants-type disposable wearing article according to claim 4, wherein the back body part further comprises a non-stretchable region adjacent to the intergluteal cleft stretchable region and outwardly on both sides of the four side edges in the width direction, and a side stretchable region, which is adjacent to the non-stretchable region at both right and left sides thereof in the width direction and extended to outer sides of both right and left side edges of the absorber in the width direction, a region, which is provided from a part of the side stretchable region on one side, through a part of the non-stretchable region on one side, the intergluteal cleft stretchable region, and a part of the non-stretchable region on the other side, to a part of the side stretchable region on the other side includes a first sheet layer, a second sheet layer and an elastic sheet forming the intergluteal cleft elastic member and being disposed therebetween, and the first sheet layer and the second sheet layer are bonded directly or indirectly at a large number of joined portions arranged at intervals, a maximum elongation in the width direction of the non-stretchable region is less than 120%, a maximum elongation of the intergluteal cleft stretchable region is 1.5 to 3 times the maximum elongation in the width direction of the non-stretchable region, a maximum elongation of the side stretchable region is 2 to 5 times the maximum elongation in the width direction of the non-stretchable region, the slots are provided only in the non-stretchable region.

10. The underpants-type disposable wearing article according to claim 1, wherein the intergluteal cleft stretchable region includes a first sheet layer, a second sheet layer and an elastic sheet disposed therebetween as the intergluteal cleft elastic member, and the first sheet layer and the second sheet layer are bonded directly or indirectly at a large number of joined portions arranged at intervals, at least in a middle part of the intergluteal cleft stretchable region in the front-back direction, an area ratio of the joined portions decreases stepwise or continuously from both a right and a left side edges of the middle part toward the center thereof in the width direction, respectively.

11. The underpants-type disposable wearing article according to claim 10, wherein the back body part further comprises a non-stretchable region adjacent to the intergluteal cleft stretchable region and outwardly on both sides of the four side edges in the width direction, and a side stretchable region, which is adjacent to the non-stretchable region at both right and left sides thereof in the width direction and extended to outer sides of both right and left side edges of the absorber in the width direction, a region, which is provided from a part of the side stretchable region on one side, through a part of the non-stretchable region on one side, the intergluteal cleft stretchable region, and a part of the non-stretchable region on the other side, to a part of the side stretchable region on the other side includes a first sheet layer, a second sheet layer and an elastic sheet forming the intergluteal cleft elastic member and being disposed therebetween, and the first sheet layer and the second sheet layer are bonded directly or indirectly at a large number of joined portions arranged at intervals, a maximum elongation in the width direction of the non-stretchable region is less than 120%, a maximum elongation of the intergluteal cleft stretchable region is 1.5 to 3 times the maximum elongation in the width direction of the non-stretchable region, a maximum elongation of the side stretchable region is 2 to 5 times the maximum elongation in the width direction of the non-stretchable region, the slots are provided only in the non-stretchable region.

12. The underpants-type disposable wearing article according to claim 1, wherein the back body part further comprises non-stretchable region adjacent to the intergluteal cleft stretchable region and outwardly on both sides of the four side edges in the width direction, and a side stretchable region, which is adjacent to the non-stretchable region at both right and left sides thereof in the width direction and extended to outer sides of both right and left side edges of the absorber in the width direction, a region, which is provided from a part of the side stretchable region on one side, through a part of the non-stretchable region on one side, the intergluteal cleft stretchable region, and a part of the non-stretchable region on the other side, to a part of the side stretchable region on the other side includes a first sheet layer, a second sheet layer and an elastic sheet forming the intergluteal cleft elastic member and being disposed therebetween, and the first sheet layer and the second sheet layer are bonded directly or indirectly at a large number of joined portions arranged at intervals, a maximum elongation in the width direction of the non-stretchable region is less than 120%, a maximum elongation of the intergluteal cleft stretchable region is 1.5 to 3 times the maximum elongation in the width direction of the non-stretchable region, a maximum elongation of the side stretchable region is 2 to 5 times the maximum elongation in the width direction of the non-stretchable region, the slots are provided only in the non-stretchable region.

13. The underpants-type disposable wearing article according to claim 1, wherein the back body part includes a third portion comprising a part of the center line passing through the center of the back body part in the width direction and located in a range configured to face a sacrum, a sacrum stretchable region bounded by two sacrum side edges and comprising a sacrum elastic member is provided over both right and left sides of the third portion in the width direction, the sacrum stretchable region stretches and contracts in the width direction between a natural length state where the sacrum elastic member is contracted, and a spread state where the sacrum elastic member is stretched, a maximum elongation in the width direction of the sacrum stretchable region is larger than a maximum elongation in the width direction of a region, which is adjacent to the sacrum stretchable region on both sides thereof in the width direction and in the absorber, on both right and left sides of the sacrum stretchable region in the width direction, slots are formed to extend outwardly in the width direction toward the back side, respectively.

14. The underpants-type disposable wearing article according to claim 13, wherein acute inclination angles between the front-back direction and directions along which the slots provided at both the right and left sides of the sacrum stretchable region in the width direction extend are 0.3 to 0.8 times the acute intersecting angles between the front-back direction and the directions along which the slots provided at both the right and left sides of the inter-gluteal cleft stretchable region in the width direction extend, respectively.

* * * * *